United States Patent [19]
Mikhail

[11] Patent Number: 5,380,331
[45] Date of Patent: Jan. 10, 1995

[54] METHOD FOR PERFORMING KNEE SURGERY AND RETRACTORS FOR USE THEREIN

[76] Inventor: W. E. Michael Mikhail, 4203 Shamley Green, Toledo, Ohio 43624

[21] Appl. No.: 915,517

[22] Filed: Jul. 20, 1992

Related U.S. Application Data

[63] Continuation-in-part of Ser. No. 508,090, Apr. 11, 1990, Pat. No. 5,217,963.

[51] Int. Cl.⁶ ............................................. A61B 17/00
[52] U.S. Cl. ........................................ 606/79; 606/86; 606/87; 606/53
[58] Field of Search .................. 606/53, 86, 87, 88, 606/89, 90, 105, 167, 172; 623/16, 20, 22, 23

[56] References Cited
U.S. PATENT DOCUMENTS

| | | | |
|---|---|---|---|
| 2,362,957 | 11/1944 | Hackett | 606/86 |
| 2,427,128 | 9/1947 | Ettinger | 606/86 |
| 2,695,607 | 11/1954 | Hipps et al. | |
| 3,731,673 | 5/1978 | Halloran | |
| 3,750,652 | 8/1973 | Sherwin | |
| 3,776,240 | 12/1973 | Woodson | |
| 3,801,989 | 4/1974 | McKee | |
| 3,955,568 | 5/1976 | Neufeld | |
| 4,147,840 | 2/1980 | Watanabe | 606/86 |
| 4,190,042 | 2/1980 | Sinnreich | |
| 4,355,631 | 10/1982 | LeVahn | |
| 4,481,947 | 11/1984 | Chester | |
| 4,501,266 | 2/1985 | McDaniel | |
| 4,520,797 | 6/1986 | Peterson | |
| 4,567,885 | 2/1986 | Androphy | |
| 4,686,972 | 9/1987 | Kurland | |
| 4,726,356 | 2/1988 | Santilli et al. | |
| 4,738,248 | 4/1988 | Ray | |
| 4,747,395 | 5/1988 | Brief | |
| 5,035,700 | 7/1991 | Kenna | |
| 5,122,144 | 6/1992 | Bert et al. | |
| 5,190,549 | 3/1993 | Miller et al. | 606/53 X |

FOREIGN PATENT DOCUMENTS

| | | |
|---|---|---|
| 462077 | 6/1980 | France . |
| 215468 | 6/1977 | Germany . |
| 3001087 | 7/1981 | Germany . |
| 1274432 | 10/1976 | United Kingdom . |
| 1445718 | 2/1978 | U.S.S.R. . |
| 1595499 | 9/1981 | U.S.S.R. . |

OTHER PUBLICATIONS

Brochure of Innomed, Inc., Mentone, IN, copyrighted 1989 entitled "Mark II Chandler Retractor".
Stille (1939) Catalog of Stainless Steel Retractors.
D. H. Levinthal, *Journal of Bone & Joint Surgery* (1931) "Knee Joint Retractors for Resections and Arthroplasties", pp. 378, 379.
Zimmer Inc. Catalog (1966), pp. 116, 117, and A163.

*Primary Examiner*—Sam Rimell
*Attorney, Agent, or Firm*—Emch, Schaffer, Schaub & Porcello Co.

[57] ABSTRACT

A lateral patellar retractor for use in performing knee surgery includes a handle, an integral flat support extending downwardly from said handle and joined to said handle by an arcuate section and a pair of integral prongs extending from said integral support in spaced apart relationship, each terminating in a pointed free, said integral prongs including a curve which is reverse of the curved path followed by said arcuate section, said support and said prongs being sized to permit the prongs to engaged the shelf of the lateral tibial condyle while said support is engaging soft tissue. Means may be provided for anchoring the support and detaching the handle.

36 Claims, 17 Drawing Sheets

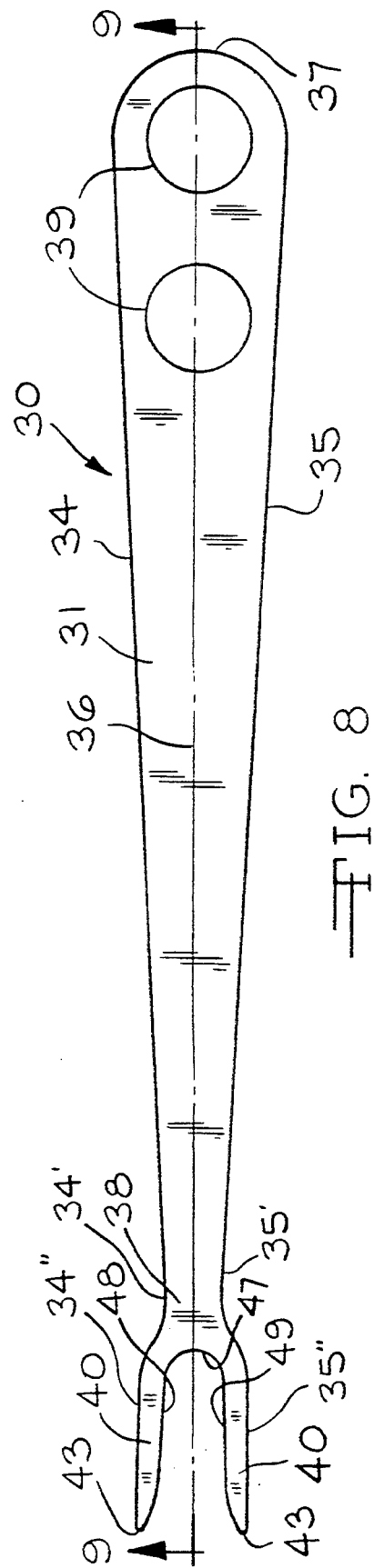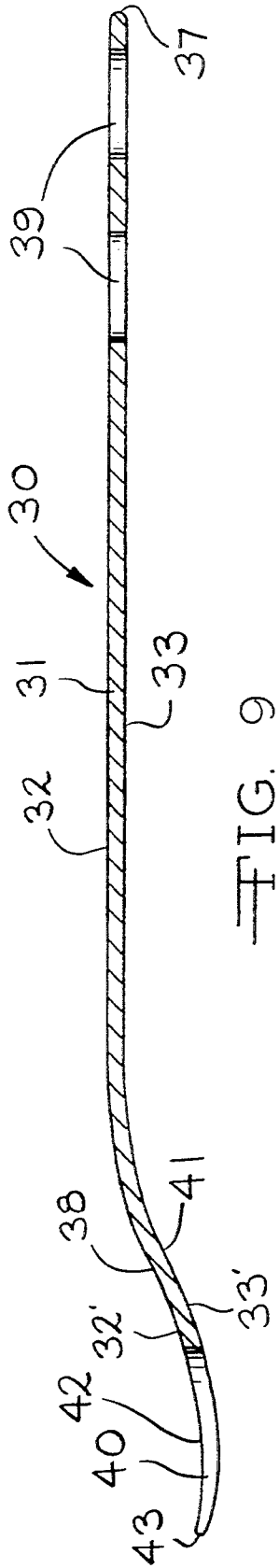

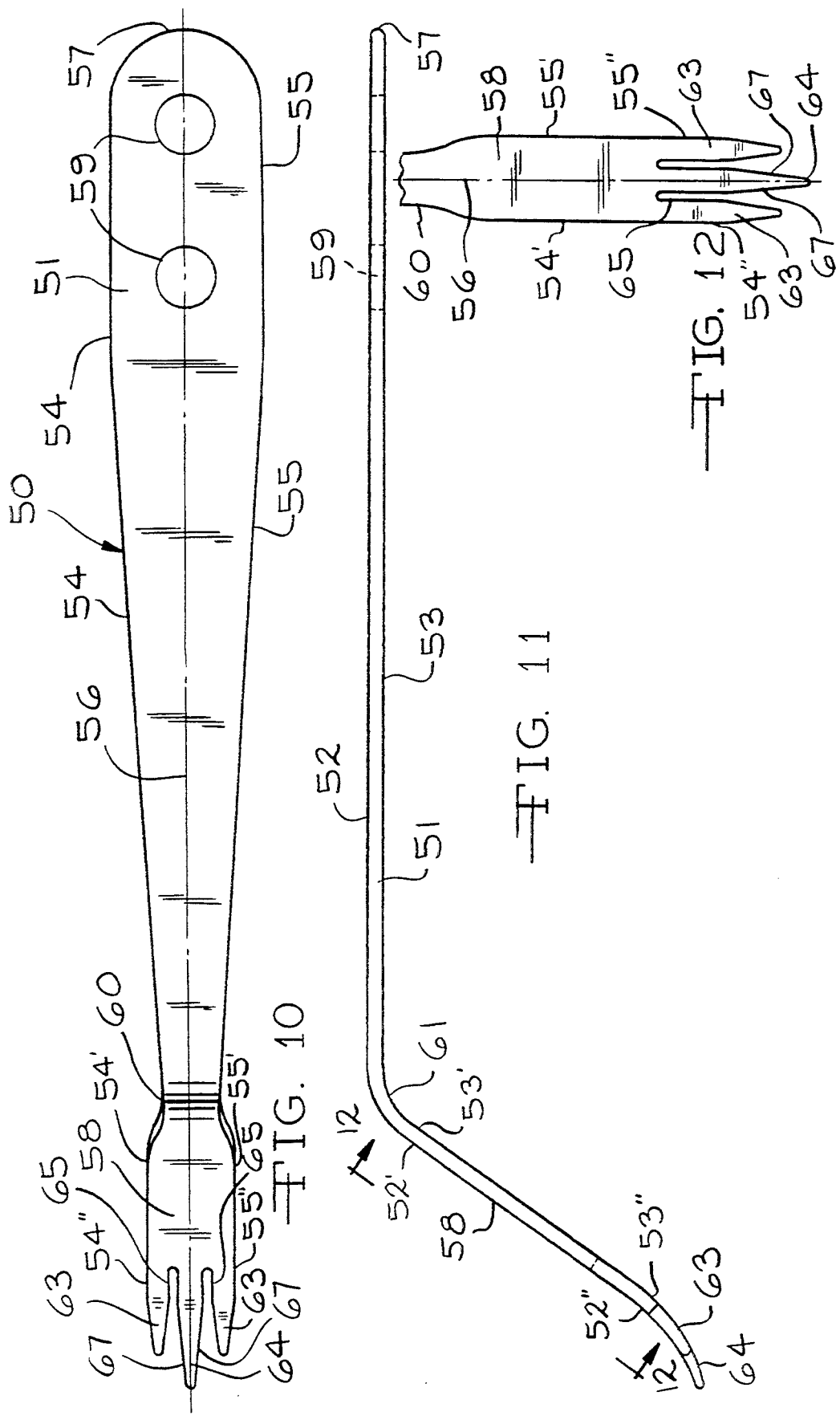

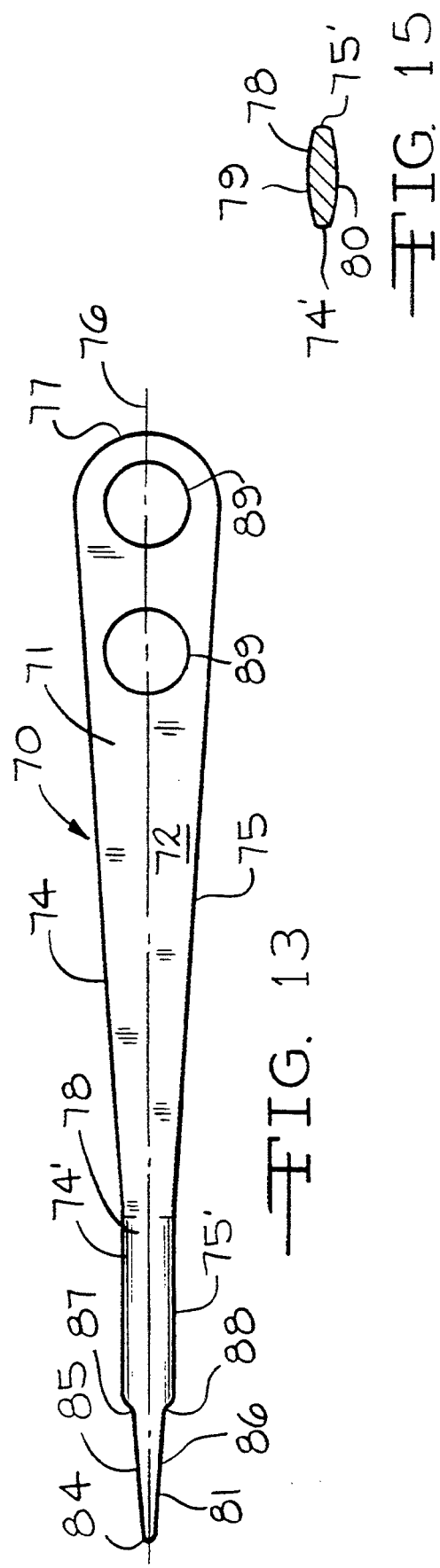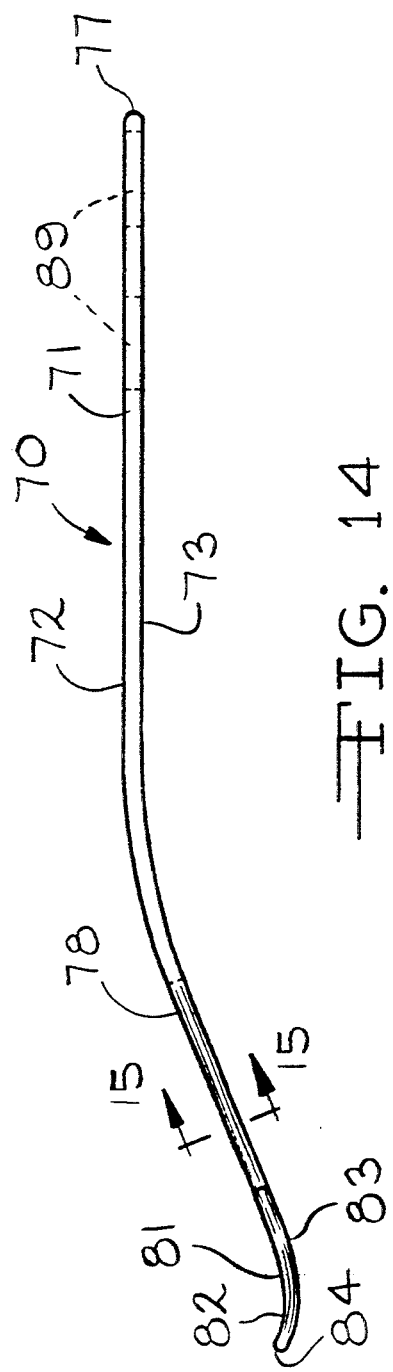

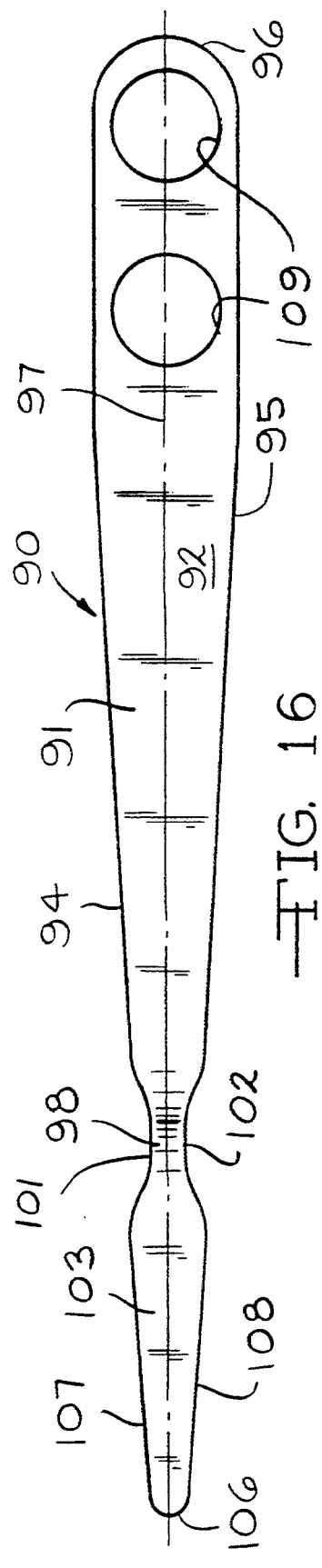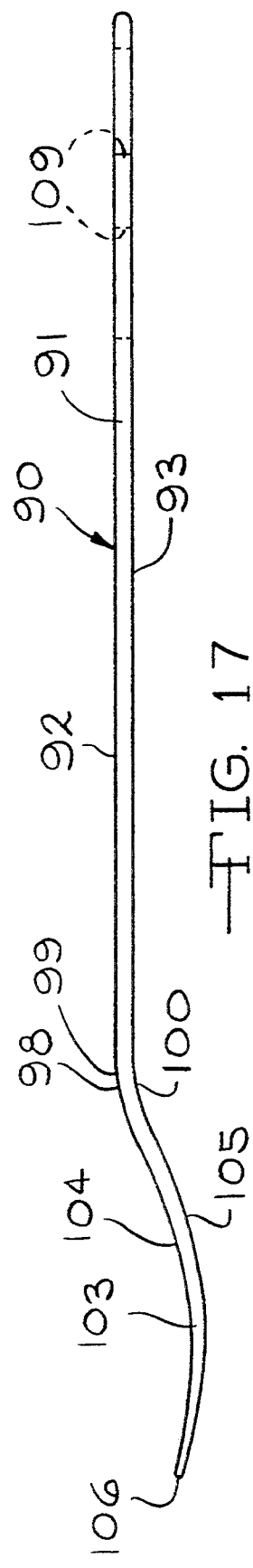
FIG. 16
FIG. 17

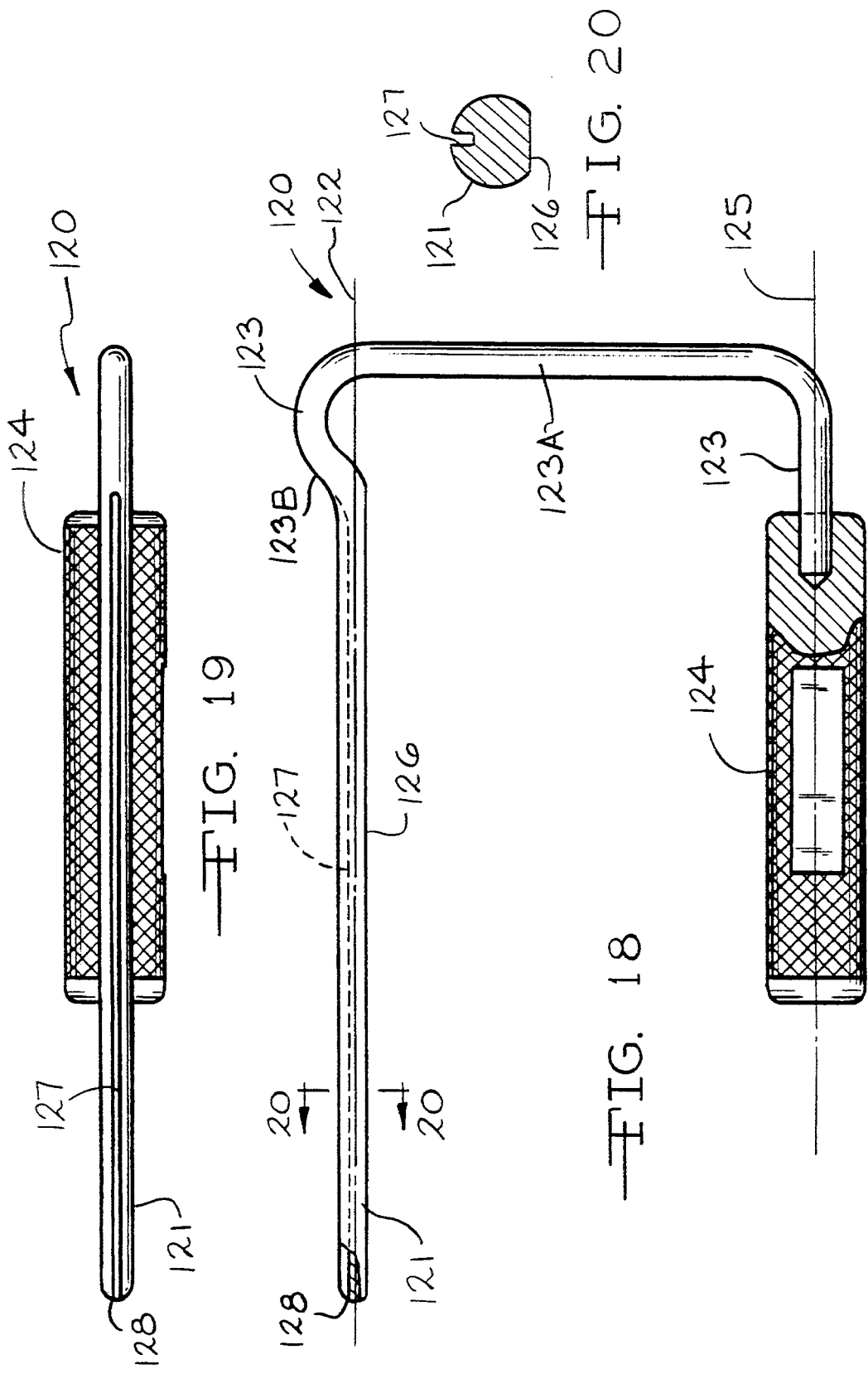

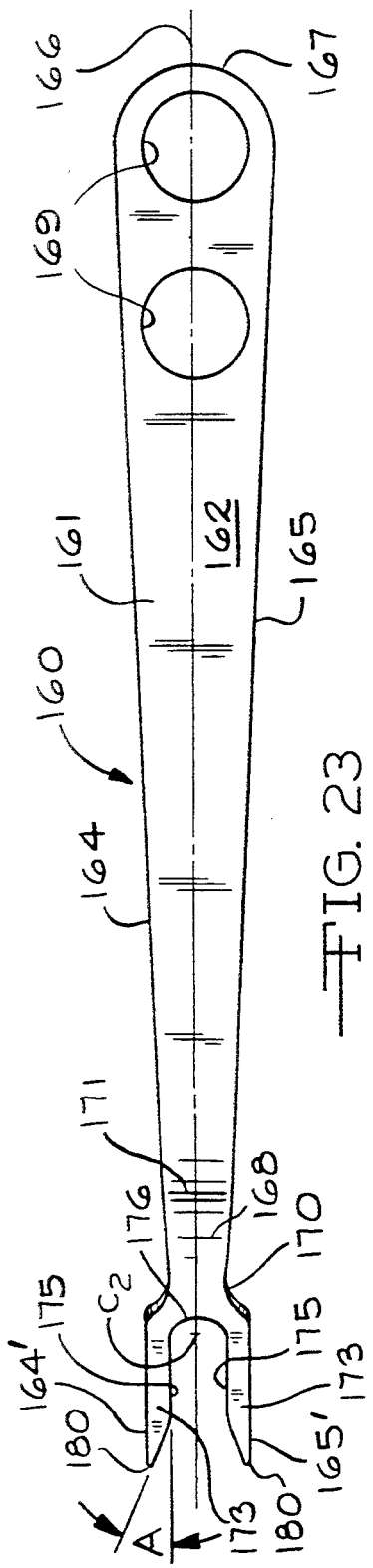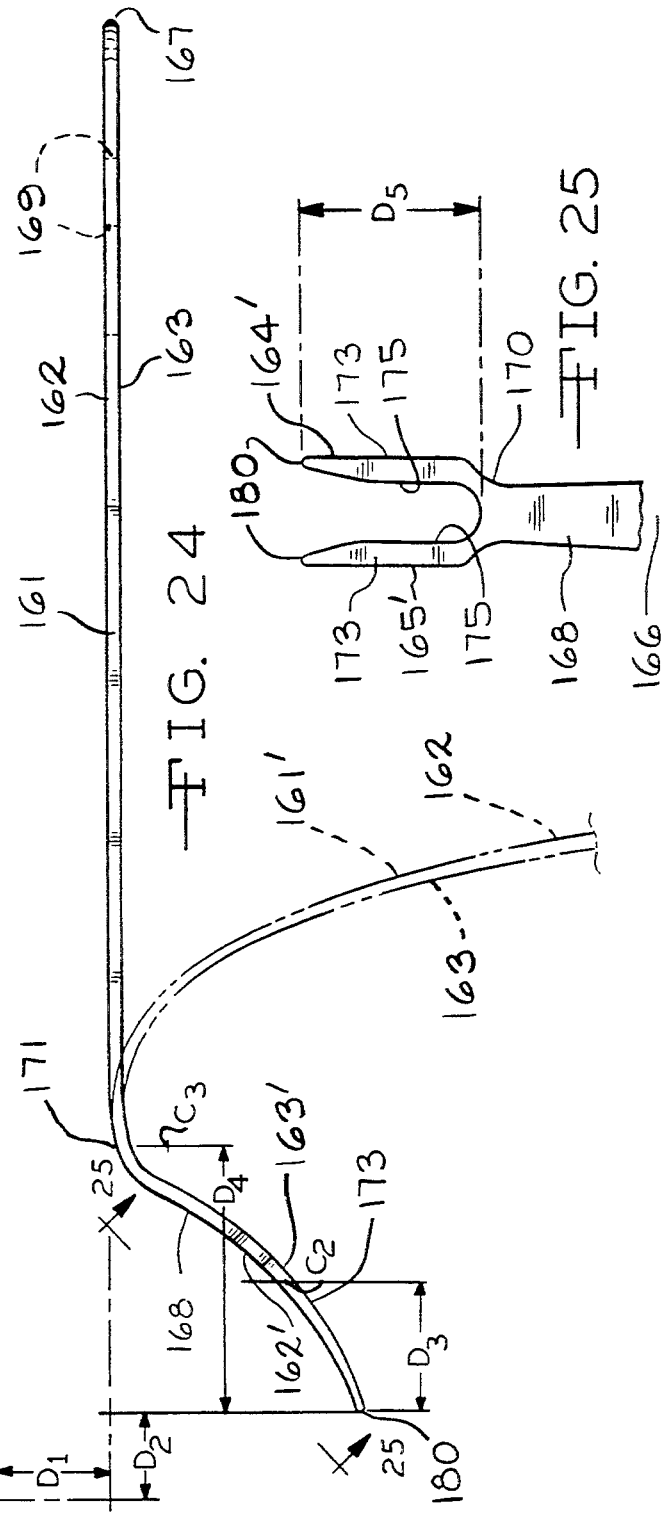

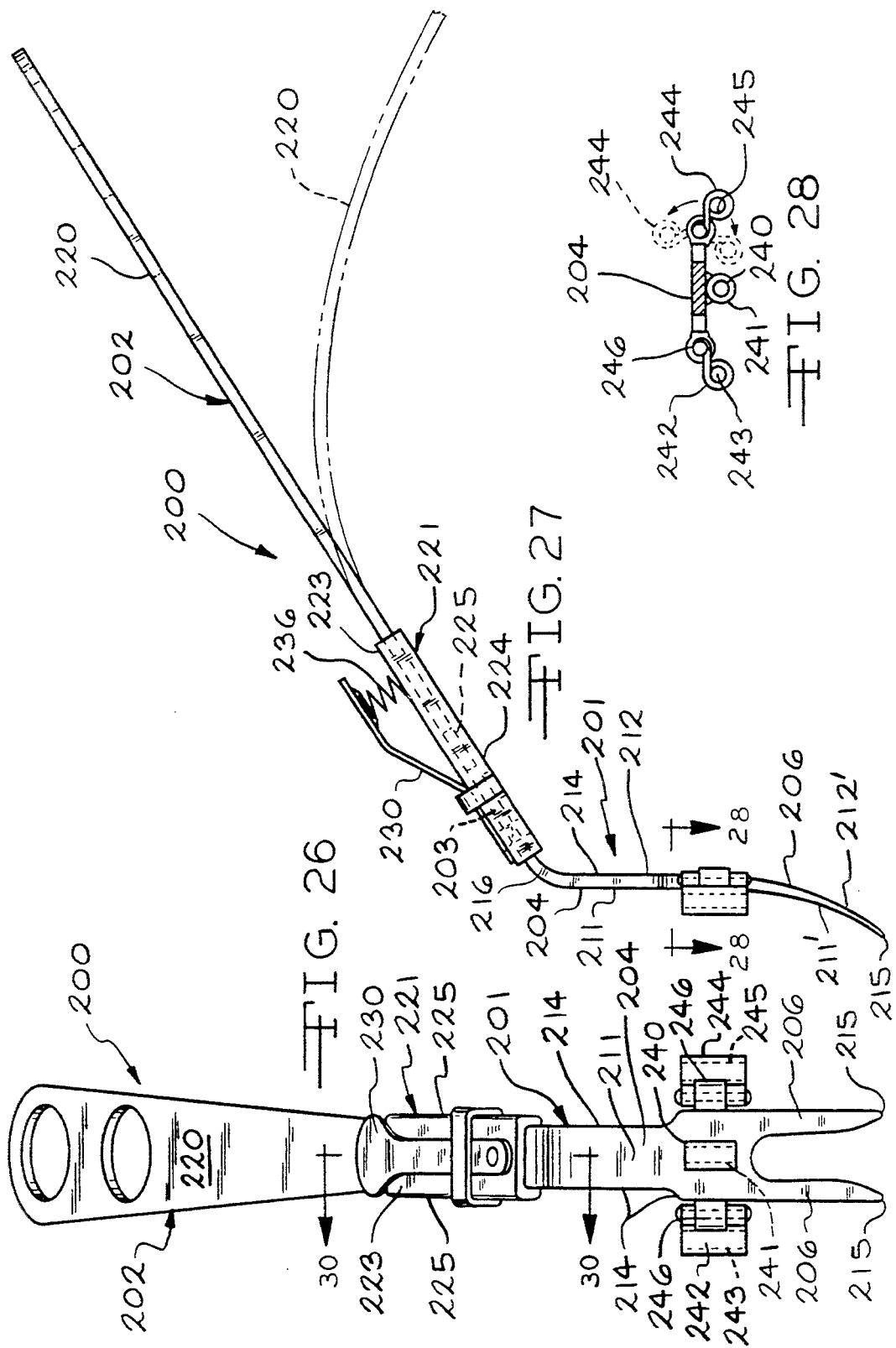

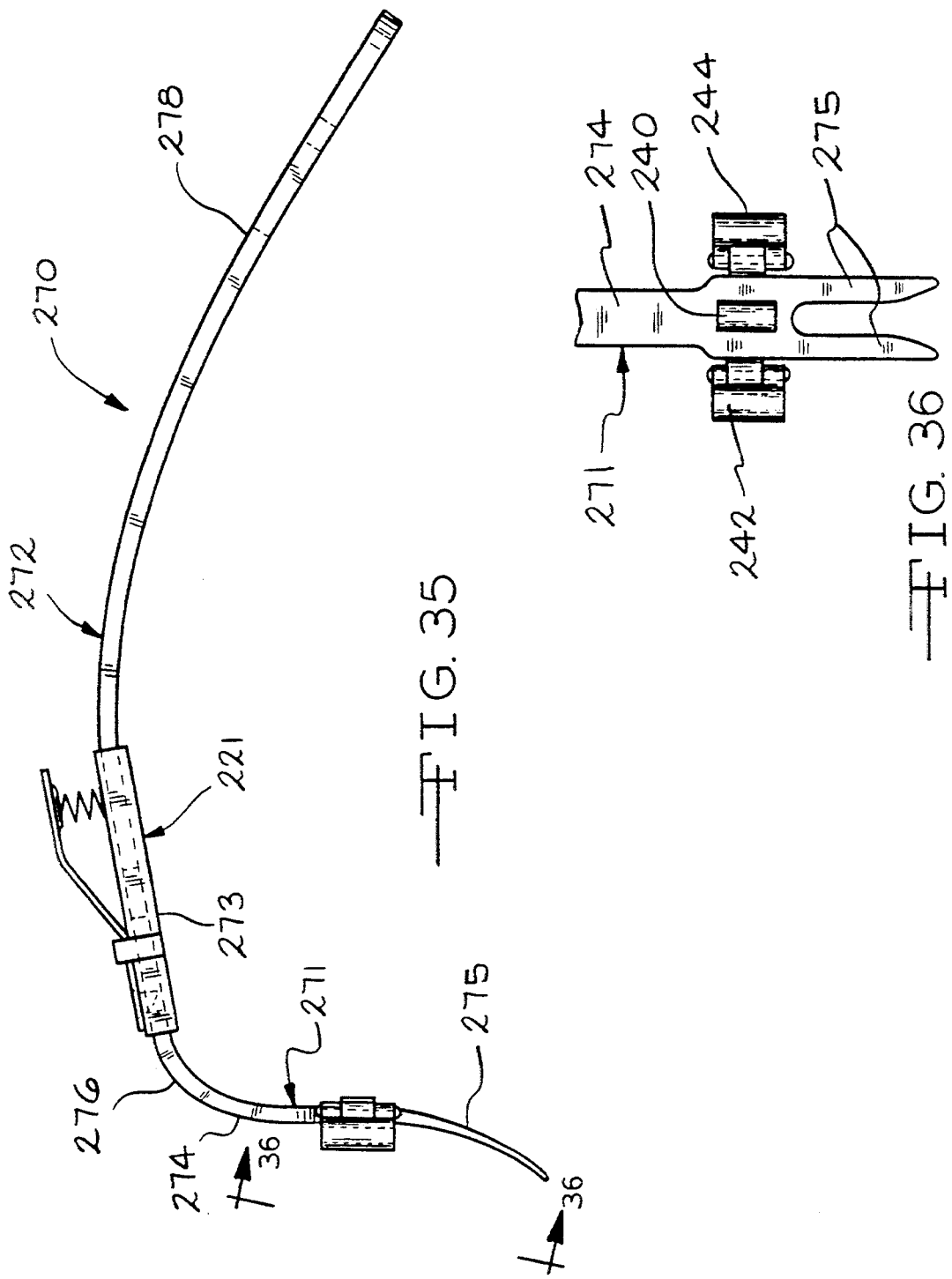

METHOD FOR PERFORMING KNEE SURGERY AND RETRACTORS FOR USE THEREIN

CROSS REFERENCE TO RELATED APPLICATION

This is a continuation-in-part of application Ser. No. 07/508,090, filed Apr. 11, 1990, now U.S. Pat. No. 5,217,963.

BACKGROUND OF THE INVENTION

In performing knee surgery it is of the utmost importance to avoid or at least minimize damage to ligaments, tendons, muscles, nerves and other portions of the soft tissue while gaining access to and performing surgical procedures on various portions of bone structure of the knee. Heretofore, the retractors utilized in performing knee surgery have not been specifically tailored to permit maximum access to the bone structure intended for osteotomy procedures while at the same time providing maximum protection for various soft tissue members.

U.S. Pat. No. 4,820,797 discloses a collateral ligament retractor for use in knee surgery. Such retractor includes a member having a cupped arcuate finger for insertion into the knee joint along and partly around the tibial plateau and a curved portion extending from the finger outwardly around the ligament, then extending back substantially in the same direction as the finger and including a downwardly extending pivoted elongated arm extending to a position behind the knee above the calf. A second member of similar design but larger to accomodate the everted patella is positioned around the opposite ligament and a tension member such as a coil spring is connected to the outer end of the arms of the members for biasing them toward one another to hold the ligaments in a retracted position.

Patentschrift No. DD-215-46Y-A of the Duetsche Demokratische Republic discloses a wound retractor for knee surgery which has a holder having a hook-shaped convex blade at the distal end.

U.S. Pat. No. 2,695,607 discloses a surgical retractor intended to hold back flesh and muscles from a bone on which surgical treatment is to be performed.

Zimmer Company, Warsaw, Indiana, Catalog for 1966 discloses on page 117 a Blount Knee Retractor having a handle with a tip disposed at an angle of more than 90° which is intended to be inserted into the knee joint just proximal to the cartilage so as to expose the line of disection while broadening out to retract the superficial soft tissue without use of an additional retractor.

None of the retractors disclosed in the above referenced prior art or any other retractors known to the applicant have the capability of providing the degree of protection as those of the present invention and no prior art surgical procedures for knee surgery are as effective in permitting access to the bone structure upon which osteotomy procedures are to be performed while providing protection to the critical soft tissue.

SUMMARY OF THE INVENTION

The present invention relates to a method of performing knee surgery and to retractors and a femoral distractor for use in performing such surgery.

BRIEF DESCRIPTION OF THE DRAWINGS

FIG. 8 is a top plan view of the PCL tibial retractor.

FIG. 9 is a sectional view taken along line 9—9 of FIG. 8.

FIG. 10 is a top plan view of the lateral patellar retractor of the present invention.

FIG. 11 is an elevational view of the lateral patellar retractor as shown in FIG. 10.

FIG. 12 is a fragmentary plan view of the retracting end of the lateral patellar retractor shown in FIG. 10 with such end rotated for clarity.

FIG. 13 is a top plan view of the posterior cruciate ligament retractor of the present invention.

FIG. 14 is a side elevational view of the posterior cruciate ligament retractor as shown in FIG. 13.

FIG. 15 is a sectional view taken through line 15—15 of FIG. 14.

FIG. 16 is a top plan view of the collateral ligament retractor of the present invention.

FIG. 17 is an elevational view of the collateral ligament retractor as shown in FIG. 16.

FIG. 18 is a top plan view, partly in section, of the femoral distractor of the present invention.

FIG. 19 is an elevational view of the femoral distractor as shown in FIG. 18.

FIG. 20 is a sectional view taken through line 20—20 of FIG. 18.

FIG. 23 is a top plan view of a modified lateral patellar retractor.

FIG. 24 is an elevational view of the modified lateral patellar retractor as shown in FIG. 23.

FIG. 25 is a fragmentary view of the retractor element of the modified lateral patellar retractor taken in the direction of line 25—25 of FIG. 24.

FIG. 26 is a top plan view of a modified lateral patellar retractor having a detachable handle.

FIG. 27 is an elevational view of the modified lateral patellar retractor as shown in FIG. 26.

FIG. 28 is a sectional view taken through lines 28—28 of FIG. 27.

FIG. 35 is an elevational view of yet another embodiment of lateral patellar retractor with detachable handle.

FIG. 36 is a fragmentary view of the retractor element looking in the direction of line 36—36 of FIG. 35.

BEST MODE FOR CARRYING OUT INVENTION

Figure 1:
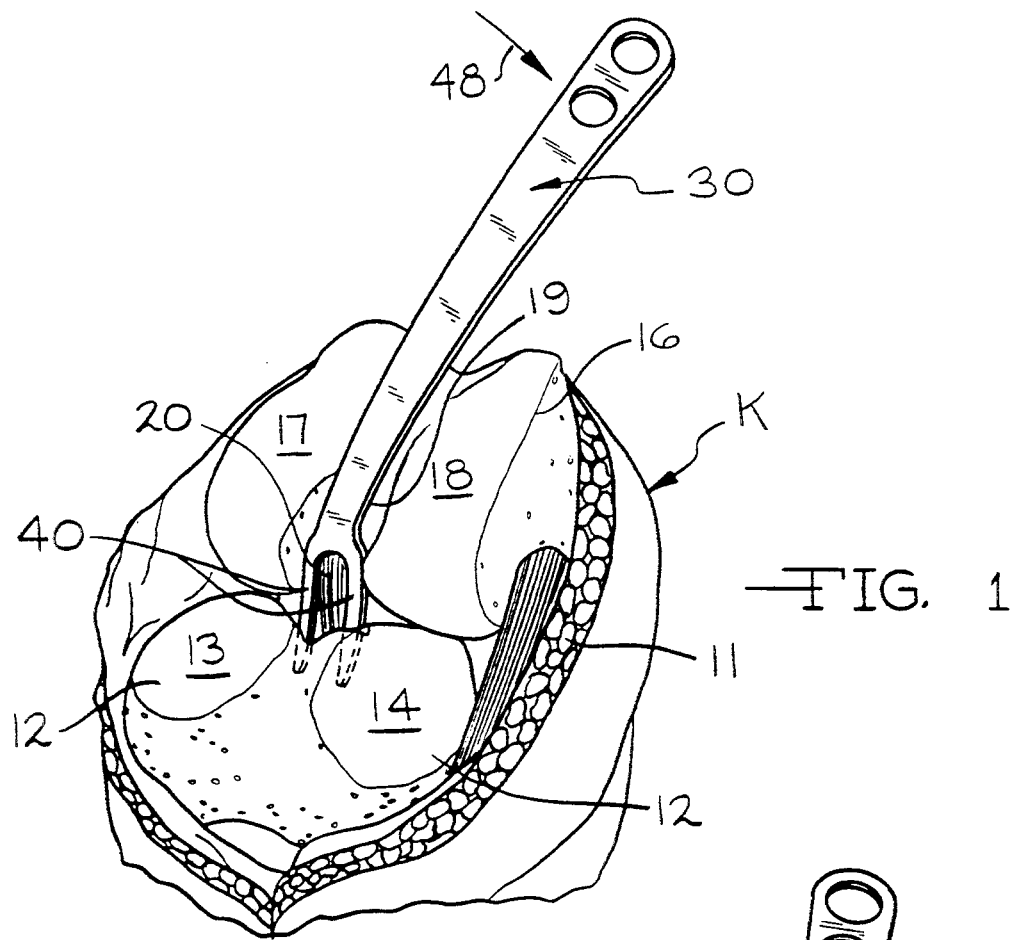
FIG. 1 is a perspective view showing a step in the knee surgery showing use of the PCL tibial retractor of the present invention.

Referring to FIGS. 1-7, there is shown a knee generally designated by the letter K in which an incision has been made through the skin and flesh 11 to expose the interior members upon which osteotomy and other procedures are to be performed. Such other procedures may include fitment and placement of an artificial knee prosthesis. Once such prosthesis is shown and described in the brochure published by Johnson & Johnson Orthopaedics, New Brunswick, New Jersey, in September 1988 entitled "P. F. C. TOTAL KNEE SYSTEM" ("P.F.C." is a registered trademark of Johnson & Johnson Orthopaedics Inc.) using a surgical technique described in a booklet published by Johnson & Johnson Products Inc. entitled "Surgical Technique—The Press Fit Condylar Total Knee System With Specialist Instrument". Although retractors will obviously be used throughout the entire surgical procedure of implanting any such prosthesis, the retractors and method defined by the present invention are directed primarily to preparation of various portions of the bone structure for receiving any such prosthesis and protection of the ligaments, tendons, muscles, nerves and other critical soft tissue members during osteotomy and other procedures.

As shown in FIGS. 1-7, the incision in the knee K permits access to the tibial plateau 12 including lateral and medial tibial condyles 13 and 14, respectively. With knee bent as shown in FIGS. 1-7 there is also exposed the distal femur 16 including lateral and medial femoral condyles 17 and 18, respectively. The intercondylar notch (femoral trochlear groove) 19 separates the lateral and medial femoral condyles 17 and 18, respectively. The posterior cruciate ligament 20 is attached to the femur and tibia proximally and distally, respectively, and needs to be completely protected during the osteotomy.

Figure 2:
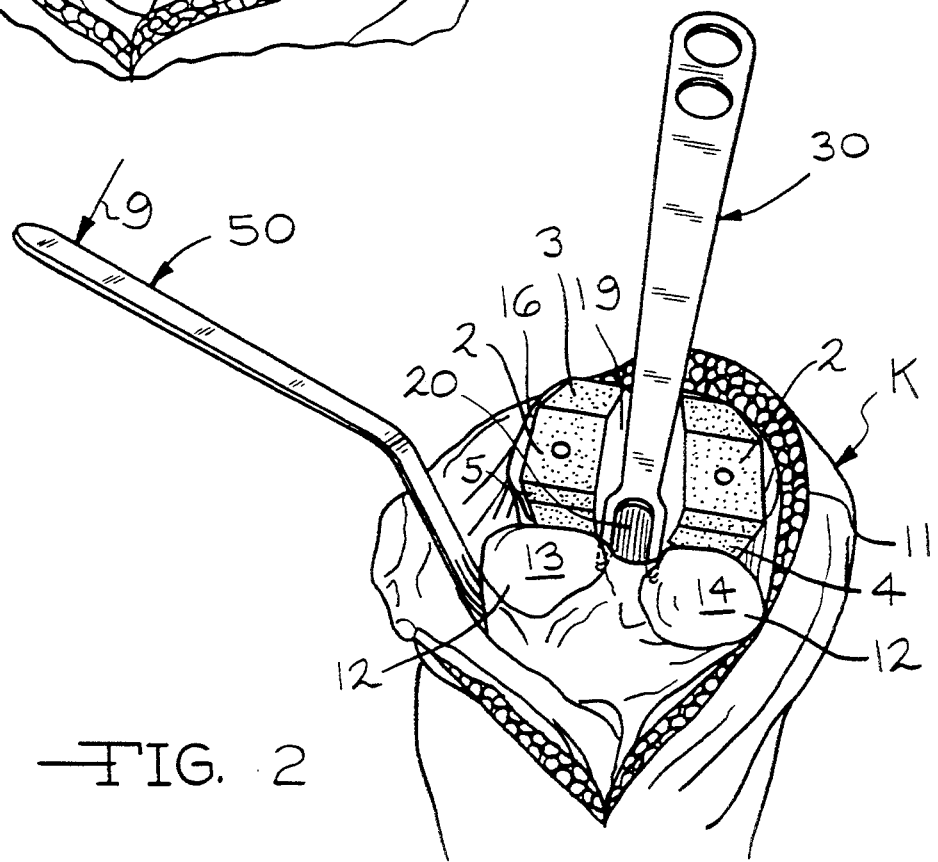
FIG. 2 is a perspective view similar to FIG. 1 showing the PCL tibial retractor and the lateral patellar retractor of the present invention in use during surgery.
Figure 3:
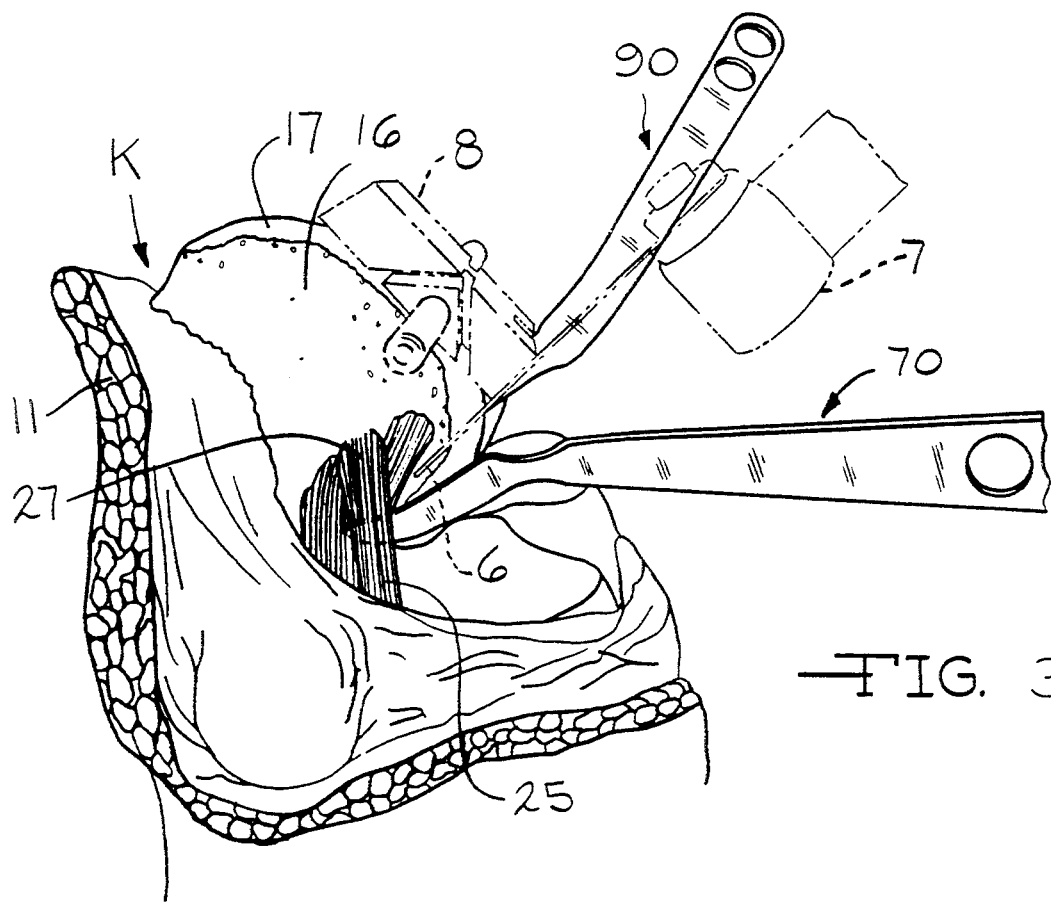
FIG. 3 is a perspective view looking from the side of a knee during surgery and showing the step of using a posterior cruciate ligament retractor and a collateral ligament retractor according to the present invention.
Figure 5:
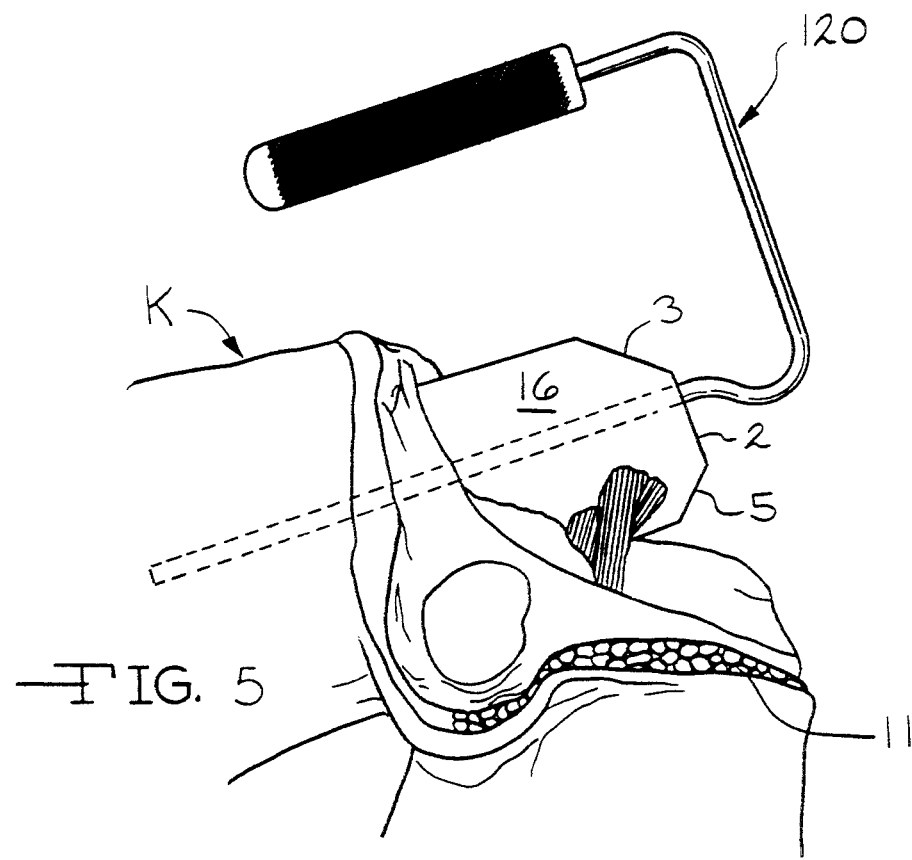
FIGS. 5 and 6 are perspective views from different angles showing the use of the femoral distractor portion of the present invention.
Figure 6:
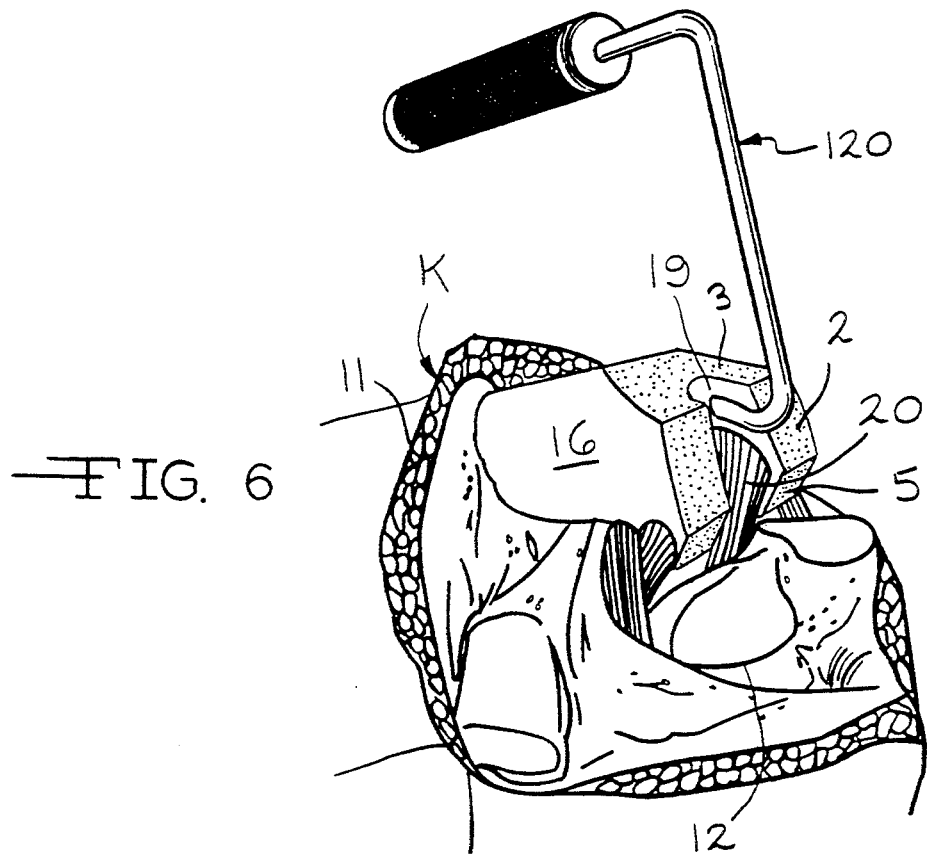
Figure 7:
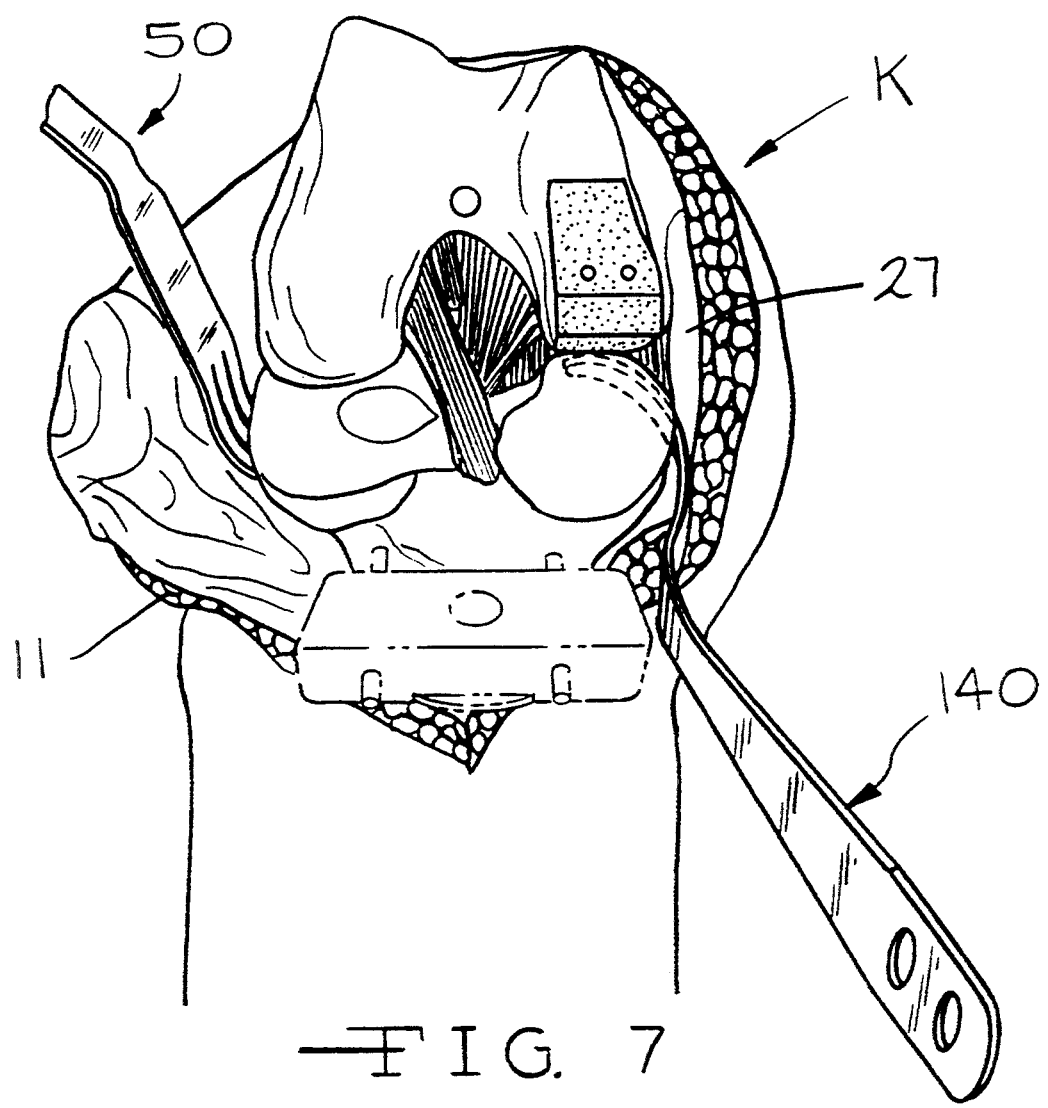
FIG. 7 is a perspective view taken from the front showing the step of using unicompartmental retractor in combination with the lateral patellar retractor.

FIGS. 2, 5 and 6 show the ,distal femur 16 following condylar osteotomies including distal femoral 2, anterior 3, posterior 4 and chamfer 5 cuts while FIG. 3 shows the position of the blade 6 of an oscillating saw 7, cutting guide 8 and PCL and collateral ligament retractors to be described hereinafter during posterior 4 femoral osteotomy. Also shown in FIG. 3 is the fibular (lateral collateral) ligament 25 which extends from The lateral aspect 27 of the lateral femoral condyle 17 to the head of the fibula (not shown). Additionally, as shown in FIG. 7, the collateral ligament 27, including its surrounding capsule is also exposed and needs to be protected during unilateral proximal tibial osteotomy.

Referring now to FIGS. 1, 2, 8 and 9, there is provided a PCL tibial retractor 30 which will be described as manufactured and as used in the surgical method herein. The PCL tibial retractor 30 includes a handle 31 which has generally flat upper and lower parallel surfaces 32 and 33, respectively, and edges 34 and 35 which taper inwardly toward each other and toward a longitudinal axis 36 from an area of maximum breadth adjacent an arcuate free end 37. The handle 31 may have one or more holes 39 to provide a place for hooking a weight thereto.

Integrally formed with the handle 31 is an integral support section 38 from which extend a pair of integral prongs 40. The support section 38 and prongs 40 will be described with the handle 31 oriented in a horizontal position. With the handle 31 so positioned, the support section 38 and prongs 40 will have an upper surface 32' and a lower surface 33' following a gentle S-shaped curve such that the support section 38 follows a curve 41 downwardly from horizontal and the prongs 40 follow a reverse curve 42 having a radius of curvature substantially the same as that of the support section and extending to ends 43 which are angled upwardly toward such horizontal plane at an angle of about 5°±2°. The lower surface 33' of the curved portion 41 has a radius of curvature of 3.312 inches±0.5 inch with its center located 3.312 inches below the lower surface 33 of the handle 31 and 3.312 inches behind the ends 43. The upper surface 32' of the curved portion 42 has a radius of curvature of 3.312 inches±0.5 inch with its center located 2.625 inches above the upper surface 32 of the handle 31 and 0.400 inch behind the ends 43. If desired, there could be a short planar segment separating the curved portion 41 from the reverse curve 42.

The PCL tibial retractor as shown in FIG. 9 has a uniform thickness of 0.120 inch throughout except for the last 0.5 inch of the prongs 40 adjacent the ends 43 each of which tapers to a thickness of 0.030 inch±0.010 inch at the ends 43. The thickness and shape of the handle are not critical; however, the handle must be sufficiently rigid to prevent excessive bending during use and must have a shape which is convenient to use without obstructing desired surgical procedures when in use.

Referring now to FIG. 8, the support section 38 includes edges 34' and 35' which taper inwardly Toward a vertical plane lying on the longitudinal axis 36 to a point of minimum breadth just before the juncture between the support section 38 and the prongs 40. This area should have a breadth of 0.430 inch±0.020 inch in order that it can fit within the intercondylar notch 19 of the femurs and to use that portion as a fulcrum without damaging it. If desired, the support section 38 could have parallel edges 34' and 35' spaced apart such distance, in which case, such edges would flare outwardly at their respective junctures with the handle 31.

As can also be seen in FIG. 8, the edges 34' and 35' join with the outer edges 34" and 35", respectively, of the prongs 40. Such outer edges 34' and 35' follow a straight line path parallel to such vertical plane lying on the longitudinal axis 36 and are spaced apart 0.770 inch±0.020 inch.

The prongs 40 have inner edges 48 and 49 which follow a straight line path in the area of juncture with said integral support section 38 and which taper outwardly from said vertical plane at an angle of 5° for the 0.5 inch portion adjacent the respective ends 43. The distance between the inner edges 48 and 49 in the straight line portion of the prongs is 0.430 inch±0.020 inch. The ends 43 are rounded with the respective tips having a breadth of 0.030 inch±0.010 inch. The inner edges 48 and 49 are joined by an arcuate segment 47, preferably having a radius of at least 0.215 inch.

As can be seen in FIGS. 1 and 2, the size, shape and space between the prongs 40 permit the prongs to straddle and thus protect the posterior cruciate ligament 20 and for the portions adjacent the ends 43 to rest against the posterior side of the respective lateral tibial condyle 13 and medial tibial condyle 14. The PCL tibial retractor 30 may then be moved in a direction toward the patient as indicated by the arrow 48 thus using the intercondylar notch 19 as a fulcrum. Such positioning presents the surfaces of the lateral tibial condyle 13 and medial tibial condyle 14 for osteotomy.

Referring now to FIGS. 2, 10, 11 and 12, there is shown a lateral patellar retractor 50 which includes a handle 51 having a longitudinal axis 56 and having generally flat upper and lower parallel surfaces 52 and 53, respectively, and edges 54 and 55. As may be seen in FIG. 10, the edges 54 and 55 are parallel to one another and to the longitudinal axis 56 in the area extending to an arcuate free end 57. The handle has one or more apertures 59 through which weighted hooks may be placed if it is desired to retain the retractor in position without a person attending thereto. Integrally formed with the handle 51 is a flat planar support section 58 which is disposed at an angle downwardly of approximately 55° from horizontal when the handle 51 is oriented in a horizontal position. Such angle could vary by as much as ±30°. An arcuate section 61 joins the support section 58 to the handle 51.

Approximately one-third of the way between the free end 57 and the arcuate section 61, the edges 54 and 55 taper inwardly toward the longitudinal axis 56 at an angle of approximately 4°. The edges 54 and 55 continue to taper inwardly toward such longitudinal axis until they reach a point of minimum breadth 60. As can be seen in FIGS. 10 and 12, the support section 58 has edges 54' and 55' which are parallel to each other and to a vertical plane lying on the longitudinal axis. Preferably the distance between such edges is about 0.71 inch; however, since its function is primarily to move the incised soft tissue away from the lateral tibial condyle 13 (see FIG. 2), it could be broader or somewhat narrower and the edges 54' and 55' are not required to be straight.

Integrally formed with and extending from the support section 58 are three prongs including a pair of side prongs 63 and a center prong 64. As can be seen from the drawings, the center prong 64 extends beyond the ends of the two side prongs 63. The prongs 63 and 64 are joined to the planar portion of the support section 58 and, as may be seen in FIG. 11 have upper and lower surfaces 52" and 53" which initially follow a straight line path and terminate in an arcuate path. The arcuate path has a radius of 1.62 inch±0.5 inch to the upper surface 52" with a center located 1.19 inch below the plane defined by the upper surface 52 of the handle 51 and 0.54 inch beyond the end of the center prong 64. The segment of the prongs 63 and 64 following a straight line path is approximately 0.35 inch while the overall length of the side prongs 63 including the portion with the straight line segment is 1.07 inch±0.020 inch while the overall length of the center prong 64 is 1.32 inch±0.020 inch. Thus, the center prong 64 extends beyond the prongs 63 by 0.25 inch.

The side prongs 63 have outer edges 54" and 55" each of which, for about 0.35 inch, are extensions of and lie in the same path followed by the edges 54' and 55', respectively, of the adjacent portion of the support section 58. Each of the side prongs 63 has an inner edge 65 which, for about 0.35 inch, is parallel to the vertical plane extending through the longitudinal axis 56. The center prong 64 has a pair of edges 67, each of which, for about 0.35 inch, is spaced from and parallel to the first portion of the inner edges 65.

The end portions of each of the prongs 63 and 64 taper to rounded tips having a radius of 0.03 inch±0.010 inch in both the horizontal and vertical planes. Thus, as can be seen in FIG. 12, the edges 54' and 65; and 55' and 65 of each of the side prongs 63, for a distance of approximately 0.72 inch from their respective ends are disposed at an angle of approximately 16° to each other. Similarly, the edges 67 of the center prong 64 for a distance of approximately 0.97 inch from its end are disposed at an angle of approximately 16° to each other.

The distance between the outer edges 54" and 55" of the side prongs 63 is 0.71 inch±0.020 inch in the area parallel to the vertical plane extending through the longitudinal axis 56 with each of such prongs having a breadth in that area of 0.18 inch. The breadth of the center prong 64 in that area in which the edges 67 are parallel is 0.20 inch.

The thickness of the lateral patellar retractor 50 is 0.12 inches throughout the entire length except for the prongs 63 and 64 which taper at their ends to a thickness of 0.06 inch±0.010 inch. The taper in thickness for the side prongs 63 and center prong 64 begins at a point 0.35 inch from their respective junctures with the support section 58 as determined by the ends of the slots between the prongs. If desired, the lateral patellar retractor 50 could have four prongs with the two center prongs extending beyond the ends of the two side prongs.

As can be seen in FIG. 2, such construction permits the lateral patellar retractor 50 to be readily inserted along side of the lateral tibial condyle 13 so that the retractor 50 may use the shelve of such lateral tibial condyle 13 as its restive point. In as much as the center prong 64 is longer than the side prongs 63, the insertion may be easily accomplished. Such elongated center prong coupled with the curved upper and lower surfaces 52 and 53 at the ends of such center prong 64 and side prong 63 permit the lateral patellar retractor 50 to slide around the lateral tibial condyle with minimum damage to the surrounding soft tissue. In particular, such configuration clearly avoids damage to the common peroneal nerve, the tibial condyle itself or the attendant lateral soft tissue structures. The broad flat support section 58 engages the lateral soft tissue structure as the handle is moved in the direction indicated by the arrow 9. Thus, when the lateral patellar retractor 50 is in such position and the PCL tibial retractor 30 is positioned as described in FIG. 1 and as shown in FIG. 2, there is provided an unimpeded presentation of the tibial plateau 12 including the lateral tibial condyle 13 and medial tibial condyle 14 with the prepared distal femoral surface 16 held safely clear of the field to allow accurate tibial osteotomy.

Referring now to FIGS. 3, 4 and 13–17, there is shown a posterior cruciate ligament retractor 70 and collateral ligament retractor 90. The posterior cruciate ligament retractor 70 includes a handle 71 which has generally flat upper and lower parallel surfaces 72 and 73, respectively, and edges 74 and 75 which taper inwardly toward the each other and toward a longitudinal axis 76 from an area of maximum breadth adjacent an arcuate free end 77. The handle 71 may have one or more holes 89 to provide a place for hooking a weight thereto. The handle 71 merges into an integral support section 78 having edges 74' and 75'. The edges 74' and 75' are parallel to a vertical plane passing through the longitudinal axis 76 assuming that the portion of the handle 71 in the area of the free end 77 is in a horizontal position.

As can be seen from FIG. 15, the support section 78 has upper and lower surfaces 79 and 80, respectively, each of which has an arcuate configuration extending from edge 74' to edge 75'. Such arcuate configuration is not critical and one or both of such surfaces 79 and 80 could be flat. The distance between the edges 74' and 75' of the integral support section 78 is 0.43 inch±0.020 inch and the thickness in the center of such support section 78 and the handle 71 is about 0.12 inch. The thickness and shape of the handle 71 and support section 78 are not critical; however, they must be sufficiently rigid to prevent excessive bending during use and must have a shape which functions to retract and protect the appropriate soft tissue without obstructing desired surgical procedures when in use.

The handle 71 curves downwardly in an arcuate path with the lower surface 73 extending through an arc of 22° with a radius of 5.0 inch±0.5 inch. The integral support section 78 extends in a generally straight line path downwardly at an angle of 22°±1.5° from horizontal.

A tip 81 is integrally formed with and extends from the integral support section 78 to an end 84. The tip 81 has upper and lower surfaces 82 and 83 which follow an arcuate path reversed from the arcuate path of the handle 71 with the upper surface 82 having a radius of 2.0 inch±0.4 inch with a center of radius located 0.78 inch above a plane defined by the upper surface 72 of the handle 71 and approximately 0.18 inch behind the end 84 of the tip 81. The length of the tip 81 from the support section 78 to the end 84 is 1.10 inch±0,020 inch. The end 84 and the portion of the tip 81 adjacent thereto are angled upwardly toward horizontal. The tip 81 has edges 85 and 86 which taper at an angle of 4°±1° to a vertical plane passing through the longitudinal axis (included angle equals 8°±2°). Each of the edges 85 and 86 flares outwardly through arcuate sections 87 and 88, respectively, in the area where the tip 81 merges with the support section 78, The edges 85 and 86 extend to the end 84 which is defined by an arcuate path having a radius of 0.05 inch±0.01 inch.

The thickness of the tip 81 tapers from 0.12 inch at the support section 78 to 0.045 inch±0.010 inch at the end 84. The end is rounded from the lower surface 83 to the upper surface 82 with a radius of 0.04 inch±0.01 inch.

Referring now to FIGS. 16 and 17, the collateral ligament retractor 90 includes a handle 91 which has generally flat upper and lower parallel surfaces 92 and 93, respectively, and edges 94 and 95. The edges 94 and 95 are generally parallel in the area adjacent an arcuate free end 96. The handle 91 may have one or more holes 109 to provide a place for hooking weights thereto. At any desired point, the edges 94 and 95 taper toward a longitudinal axis 97. The handle 91 merges into an integral support section 98. The integral support section 98 includes upper and lower surfaces 99 and 100, respectively, which curve downwardly following a curved path through an arc of approximately 28° on a radius of approximately 1.25 inches from the lower surface 100. The support section 98 has edges 101 and 102 which follow a straight line path parallel to a vertical plane passing through the longitudinal axis 97 and flare outwardly where they are joined to edges 94 and 95, respectively, of the handle 91. The breadth of the support section 98 in the area in which the edges 101 and 102 follow a straight line path is 0.24 inch±0.020 inch.

A tip 103 extends from the integral support section 98 to a blunt free end 106. The tip 103 has upper and lower surfaces 104 and 105, respectively, which follow a curved path through an arc of 44.5°±0.5° and having a radius of 3.0 inches, the center of which is 2.5 inches±0.5 inch above a horizontal plane defined by the upper surface 92 of the handle and positioned 0.88 inch behind the end 106 of the tip 103. Thus, as can be seen, the tip 103 has its end 106 pointed slightly upwardly toward the horizontal plane defined by the upper surface 92; however, it does not extend up to such plane. At its lowest point, the tip 106 is approximately 0.59 inch below such horizontal plane.

The tip 103 has edges 107 and 108, respectively, which taper inwardly toward a vertical plane passing through the longitudinal axis 97 at an angle of 4°±1° and joining the end 106 which has a radius of 0.125 inch±0.010 inch. Thus the included angle between the edges is 8°±'° the tip 103 has a maximum breadth 0.41 inch±0.02 inch located 1.93 inch from the end 106. The breadth near the end 106 at the point of juncture between the straight line segment of the edges 107 and 108 and the arcuate tip is 0.25 inch±0.02 inch.

The collateral ligament retractor 90 has a thickness of 0.12 inch throughout the handle portion 91 and the integral support section 98 and tapers to a thickness of 0.09 inch±0.02 inch at the end 106 with the end rounded in the vertical direction on a radius of 0.045 inch±0.01 inch. The thickness and shape of the handle 91 and the thickness of the support section 98 are not critical; however, they must be sufficiently rigid to prevent excessive bending when in use and must have a shape which functions to retract and protect the appropriate soft tissue without obstructing surgical procedures when in use.

Referring now to FIGS. 5, 6 and 18–20, there is shown a femoral distractor 120 for use in providing traction to the femur during surgery. Such distraction opens the joint to enhance visualization of the posterior capsule and facilitate removal of osteophytes, loose bodies and residual meniscal tissue. Such distraction also assists in accurate evaluation of the flexian gap. The femoral distractor 120 of the present invention permits the surgeon to provide maximum traction with minimized possibility of damage and ease of insertion into the medullary canal of the femur and includes vent means provided to relieve pressure during such insertion.

The femoral distractor 120 includes an insertion rod 121 following a straight line path along a longitudinal axis 122, a generally U-shaped support rod 123 integrally formed therewith and a handle 124 joined to support rod 123 along a second longitudinal axis 125 parallel to and spaced from the longitudinal axis 122.

The insertion rod 121 may have a circular cross-sectional configuration but preferably has a cross-sectional configuration such as that shown in FIG. 20, which can best be described as a circular cross-sectional configuration from which a chordal segment has been removed to provide a flat planar surface 126 in the area facing toward the handle 124.

The insertion rod 121 is also provided with a longitudinal groove 127 extending parallel to the longitudinal axis 122 from a rounded free end 128 to The juncture of the insertion rod 121 with the support rod 123. The groove 127 is positioned opposite the flat planar face 126 and provides a vent passageway to relieve pressure as the insertion rod is inserted into the medullary canal of the femur.

A significant feature of the femoral distractor 120 of the present invention resides in the configuration of the support rod 123 in the area of its juncture with the insertion rod 121. Thus, as shown most clearly in FIG. 18, a major portion 123A of the support rod 123 is disposed at an angle of 90° to the respective longitudinal axes 122 and 125. The portion forming the corner 123B initially follows an arcuate path in a direction away from both of said longitudinal axes 122 and 125 followed by a reverse curved portion joining it to the major portion 123A. Such construction permits the surgeon to apply the needed pressure required for maximum distraction under the circumstances while ensuring against undue pressure being placed against that portion of the femur adjacent the entry point of insertion into the medullary canal. Thus, construction of the support rod 123 with the outwardly bent corner 123B which initially extends away from the longitudinal axis 125 on which the handle is placed appears to provide for a more uniform distribution of the stresses over a large portion of the femur during distraction. In contrast, a distractor which follows a simple arcuate 90° path from the insertion rod to the support rod appears to concentrate; excessive pressure at that portion of the femur immediately adjacent the point of insertion into the medullary canal. Such excessive pressure may also occur when distraction is performed by lifting the protruding end of a straight insertion rod which had been placed in the medullary canal.

Figure 21:
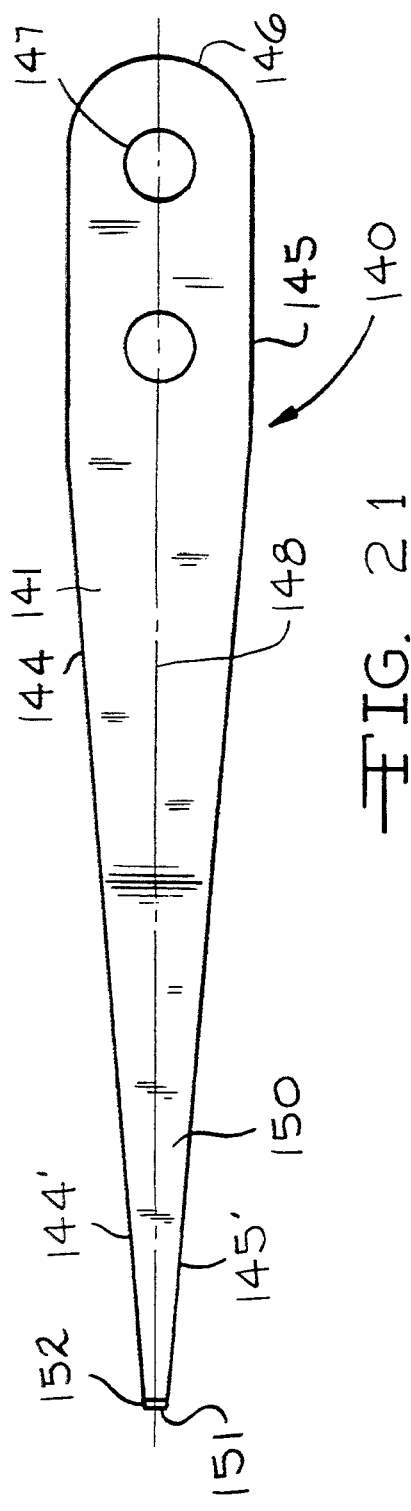
FIG. 21 is a top plan view of the unicompartmental retractor of the present invention.
Figure 22:
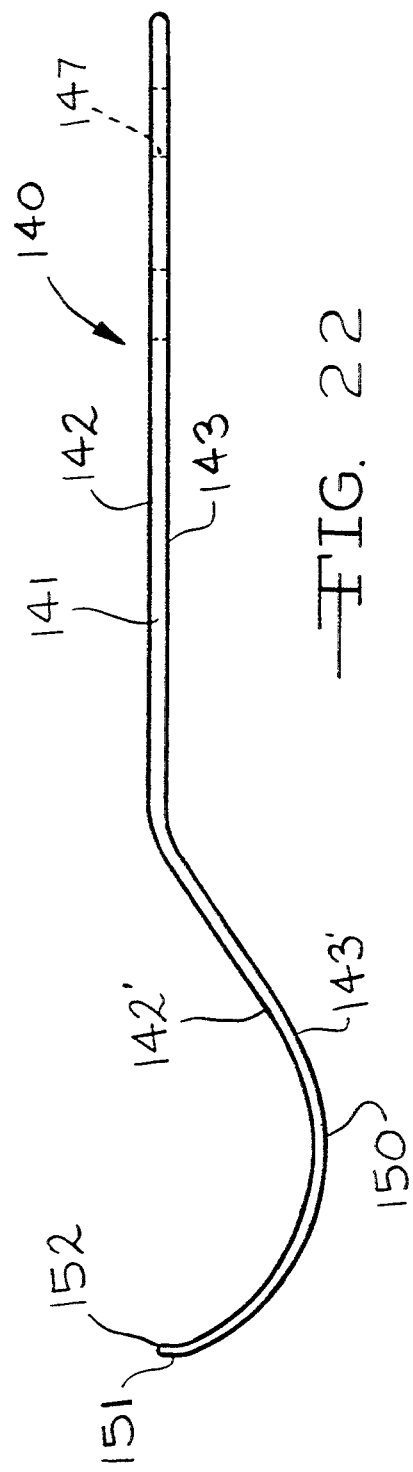
FIG. 22 is an elevational view of the unicompartmental retractor as shown in FIG. 21.
Figure 29:
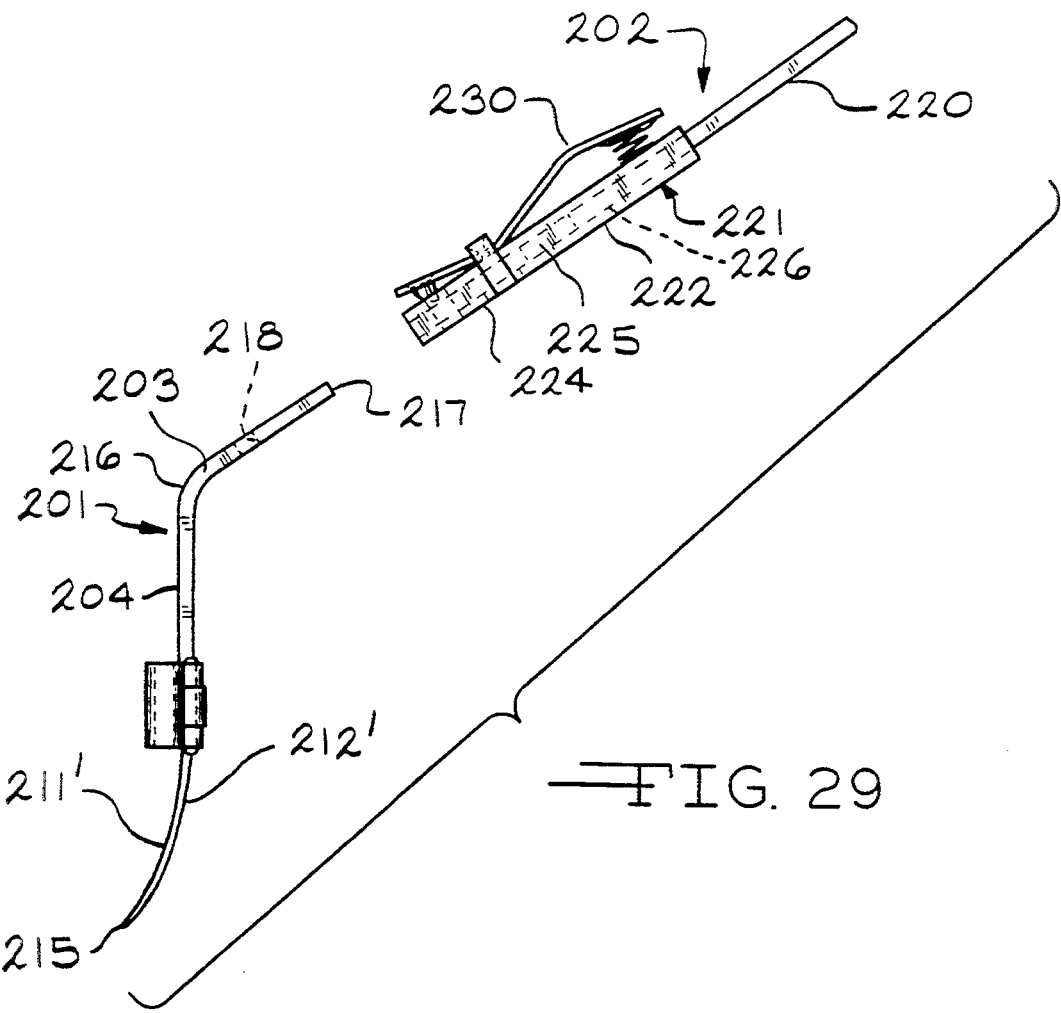
FIG. 29 is an elevational view of the modified lateral patellar retractor of FIG. 26 showing the handle detached from the retractor element.

Referring now to FIGS. 7, 21 and 22, there is provided a unicompartmental retractor 140 which is designed as a shield to protect the collateral ligament 27 and posterior structures during unilateral proximal tibial osteotomy.

The unicompartmental retractor includes a handle 141 which has generally flat upper and lower parallel surfaces 142 and 143, respectively, and edges 144 and 145. The edges 144 and 145 are generally parallel in the area adjacent an arcuate free end 146. The handle 1 41 may have one or more holes 147 to provide a place for hooking weights thereto. At any desired point, the edges 144 and 145 may taper toward a longitudinal axis 148.

Extending from the handle is an integral tip 150 having edges 144' and 145' which continue to taper toward a vertical plane passing through the longitudinal axis 148 (assuming the handle 141 is positioned with the upper and lower surfaces 142 and 143 in a horizontal plane). The tip 150 has upper and lower surfaces 142' and 143', respectively, which initially follow a straight line angled path downwardly from the handle 141 at an angle of approximately 45°±1.5°. It then joins with an arcuate portion where it curves upwardly on a radius of 1.5 inches±0.2 inch. The center of radius of such arc is positioned 0.35 inch±0.2 inch above the plane defined by the upper surface 142 of the handle and 2.26 inches±0.05 inch forward of the juncture of the tip 150 with the handle 141. The arcuate section of the tip 150 has extending therefrom a short straight segment 151, 0.30 inch±0.02 inch in length, which is disposed at an angle of 5°±2° from vertical in a direction away from said handle 141 and terminates in an end 152 approximately 0.10 inch below the plane of the upper surface 142. The end 152 has a breadth of 0.30 inch±0.020 inch and preferably is rounded from the surface 142' to the surface 143'.

The handle 141 and the tip 150 up to approximately its lowest point of the arcuate section have a thickness of approximately 0.12 inch. However, the thickness in that area is not critical provided it is rigid enough to prevent excessive bending during use. From such lowest point to the end the thickness of the tip 150 tapers with a thickness at the end 152 of 0.060 inch±0.020 inch.

The angle of taper of the edges 144' and 145' is 5°±1° from a vertical plane passing through the longitudinal axis 148 for a total included angle of 10°±2°.

In conducting the surgical procedure according to the method of the present invention, following incision of the knee K, the PCL tibial retractor 30 is inserted carefully between the distal femur 16 and the tibial plateau 12 with the prongs straddling on opposite sides of the posterior cruciate ligament 20 with the ends 43 of the prongs 40 resting against the posterior side of the lateral tibial condyle 13 and medial tibial condyle 14, respectively. The support section 38 of the PCL tibial retractor rests against the intercondylar notch 19 which acts as a fulcrum as the handle 31 is moved in the direction indicated by the arrow 48.

The lateral patellar retractor 50 is then inserted using the elongated center prong 64 as the lead along the lateral aspect of the lateral tibial condyle 13 with the support section 58 moving the adjacent soft tissue away from the incision to permit tibial osteotomy without risking damage to the surrounding soft tissue.

After performing osteotomy on the tibial plateau, namely, the lateral tibial condyle 13 and medial tibial condyle 14, the posterior cruciate ligament retractor 70 is inserted on the medial side of the medial femoral condyle 18 while the collateral ligament retractor 90 is passed around the opposite side of such medial femoral condyle 18 meeting posteriorly to form a protective arc to protect the ligaments and hold them clear of the blade of the oscillating saw during osteotomy of the posterior portion of the medial femoral condyle 18. The instruments are reversed and placed around the lateral femoral condyle 17 during posterior osteotomy of such lateral femoral condyle.

The unicompartmental retractor 140 is inserted around the side and posterior aspect of the tibial condyle, either the lateral tibial condyle 13 or medial tibial condyle 14, in order to protect the collateral ligament and posterior structures during unilateral proximal tibial osteotomy.

Referring now to FIGS. 23, 24 and 25, there is shown a modified lateral patellar retractor 160 which includes a handle 161 extending along a longitudinal axis 166 and having an upper surface 162, a lower surface 163 parallel thereto and edges 164 and 165. The handle has one or more apertures 169 through which weighted hooks may be placed if it is desired to retain the retractor in position without a person attending thereto. Preferably at least a portion of the upper and lower surfaces 162, 163 are flat or planar as shown in solid lines in FIG. 24; however, They could follow a curved path as shown in dashed lines in FIG. 24. Integrally formed with the handle 161 is a support section 168 having a short planar portion which is disposed at an angle downwardly from horizontal of approximately 55° when the handle 161 is flat or planar and oriented in a horizontal position. Such angle may vary by as much as ±30°. The length of the planar portion of the support section is 0.702 inch±0.030 inch. An arcuate section 171 having a radius of 0.5 inch±0.030 inch measured to the lower surface 163 joins the planar portion of the support section 168 to the handle 161.

If the handle 161 is curved such that its upper and lower surfaces 162, 163 follow a curved path, for example, as shown in phantom lines in FIG. 24, the downward angle of the planar portion of the support section 168 may be measured from a plane which is tangent to that portion of the upper surface 162 which is 35°±5° around the curve of the arcuate section 171 from the point of tangency between such arcuate section 171 and the planar portion of the support section 168.

As may be seen in FIG. 23, the edges 164 and 165 extend from an arcuate free end 167 along a straight-line path tapering toward one another to the arcuate section 171 joining the support section 168 to the handle 161. In the area of the support section 168, the edges 164 and 165 continue to taper inwardly toward each other until they reach a point of minimum breadth 170. The distance between such edges 164 and 165 at the point of minimum breadth 170 is approximately 0.43 inch±0.030 inch; however, since a part of the function of the support section 168 is to move the incised soft tissue away from the lateral tibial condyle, such minimum breadth could be broader or somewhat narrower. Reference is made to the portion of the specification describing the embodiment of lateral patellar retractor 50 shown in FIGS. 10, 11 and 12 and its use as shown in FIG. 2.

Integrally formed with and extending from the support section 168 are a pair of prongs 173. As may be seen in FIG. 24, the prongs 173 have upper and lower surfaces 162' and 163' which initially follow an arcuate path. The prongs 173 each extend to a tip 180. The arcuate path has a radius of 3.31 inch±0.015 inch to the upper surface 162' with a center C located a distance $D_1$ 1.06 inch±0.015 above the plane defined by the upper surface 162 of the handle 161 and a distance $D_2$ 1.45 inch±0.015 beyond the end of the prongs 173 as measured along said plane from a second plane perpendicular thereto and passing through said tips 180.

In the preferred embodiment, the arcuate path of each of the prongs 173 extends throughout an arc of approximately 20°. The portion of each of the prongs 173 from the tip 180 for a distance of 0.501 inch±0.030 inch follows a planar path. If desired, however, the prongs 173 could follow the arcuate path with the radius of 3.31 inch±0.015 inch as previously described throughout their entire lengths. As can be seen from FIG. 24, the upper surface 162' of the prongs 173 follows a concave path as viewed in elevation and the lower surface 163' of the prongs 173 follows a convex path.

The prongs 173 have outer edges 164' and 165' which are parallel. The distance between the outer edges 164' and 165' is 0.770 inch±0.005 inch. Each of the prongs 173 has an inner edge 175. The inner edges 175 are parallel and spaced apart 0.430 inch±0.005 inch throughout a major portion of their length adjacent the support section 168.

The end portions of each of the prongs 173 taper to rounded tips 180 having a radius of 0.03 inch±0.010 inch in both the horizontal and vertical planes. As can be seen in FIGS. 23 and 25, the inner edges 175 of each of the prongs 173, for a distance of approximately 0.500 inch±0.005 inch from their respective tips 180 are disposed at an angle A of approximately 13° from the line of the inner edges 175.

The inner edges 175 are joined by an arcuate segment 176 having a radius of 0.21 5 inch±0.005 inch the center $C_2$ of which lies on a line positioned a distance $D_3$ 1.14 inch±0.015 inch from a plane extending through the tips 180 and perpendicular to the plane defined by the handle 161. As will be appreciated, this distance will vary as the angle of the planar portion 168 of the support section varies. Thus, the actual length of the prongs 173 from the tips 180 to the back of the arcuate portion is 1.68 inch±0.030 inch. This is the distance $D_5$ when the prongs 173 are oriented as shown in FIG. 25.

The center $C_3$ of radius for the arcuate section 171 is 0.50 inch±0.030 inch below the lower surface 163 and a distance $D_4$ 2.18 inches±0.030 inch from a plane extending through the tips 180 and perpendicular to the plane defined by the handle.

The thickness of the modified lateral patellar retractor 150 is 0.12 inch±0.015 inch throughout the entire length except for the prongs 173. The prongs 173 Taper throughout their respective lengths from 0.12 inch±0.015 inch in the area of the arcuate segment 176 to a thickness of 0.06 inch±0.005 inch at their tips 180.

As with the embodiment of FIGS. 10-12, the modified lateral patellar retractor 160 of the present embodiment may be readily inserted along side of the lateral tibial condyle 13 so that the retractor 160 may use the shelve of such lateral tibial condyle 13 as its restive point. The spaced apart prongs 173 with their tapered end portions adjacent the tips and their curved upper and lower surfaces 162' and 163' permit the lateral patellar retractor 160 to slide around the lateral tibial condyle with minimum damage to the surrounding soft tissue. In particular, such configuration clearly avoids damage to the common peroneal nerve, the tibial condyle itself or the attendant lateral soft tissue structures. The broad support section 168 engages the lateral soft tissue structure as The handle is moved in the direction indicated by the arrow 9 in FIG. 2. Thus, when the modified lateral patellar retractor 160 is in such position and the PCL tibial retractor 30 is positioned as described in FIG. 1 and as shown in FIG. 2, there is provided an unimpeded presentation of the tibial plateau 12 including the lateral tibial condyle 13 and medial tibial condyle 14 with the prepared distal femoral surface 16 held safely clear of the field to allow accurate tibial osteotomy.

Referring now to FIGS. 26–36, there is shown a modified lateral patellar retractor 200 which includes a retractor element 201 and a detachable handle 202.

The retractor element 201 includes an attachment section 203 and an integral support section 204 from which extend an integral pair of prongs 206. The support section 204 includes an upper surface 211, a lower surface 212 and a pair of edges 214 extending between the upper and lower surfaces. As in the embodiment of FIGS. 23-25, the prongs 206 are spaced apart and follow an arcuate path throughout a major portion of their length such that their upper surfaces 211' are concave and their lower surfaces 212' are convex. The prongs 206 each extend to a tip 215. Preferably, the arcuate path and dimensions are similar to that set forth in the embodiment of FIGS. 23–25.

The upper and lower surfaces 211 and 212 of the support section 204 follow a planar path in the area adjacent the prongs 206 followed by a curved path forming a reverse bend 216 and finally a planar path in the area between the reverse bend 216 and the attachment section 203. By reverse bend it is meant that, as viewed in elevation, the bend or curve is in a direction generally opposite that of the prongs 206 in that in the area of reverse bend 216, the upper surface 211 is convex and the lower surface 212 is concave. This is, of course, opposite from the path followed by the upper and lower surfaces 211' and 212' of the prongs 206 in which the upper surface 211' is concave and the lower surface 212' is convex. The attachment section 203 extends to an end 217 and is provided with an aperture 218 the function of which will become readily apparent from the following description of the detachable handle 202.

The detachable handle 202 includes a gripping element 220 and a connecting element 221 permanently secured thereto. The connecting element 221 includes a housing 222 having upper and lower wall members 223 and 224, respectively, joined together by edges 225 cooperating to define a passageway 226 extending therethrough. The gripping element 220 is permanently mounted in the housing 222 with minor portion positioned in the passageway 226 and a major portion extending out of the passageway as shown in FIG. 27. Additionally, as shown in FIG. 27, the entire gripping element 220 could be planar or it could be curved downwardly as shown in phantom lines in FIG. 27.

The relative sizes of the passageway 226 and the portion of the attachment section 203 adjacent the end 217 are such as to permit the section 203 adjacent such end to be slideably received in such passageway 226. A stop member 228 extends through the lower wall 224 of housing 222 and into the passageway 226 in a position to be engaged by the end 217 and to thus limit the extent to which the attachment section 203 may be inserted into such passageway 226.

Figure 30:
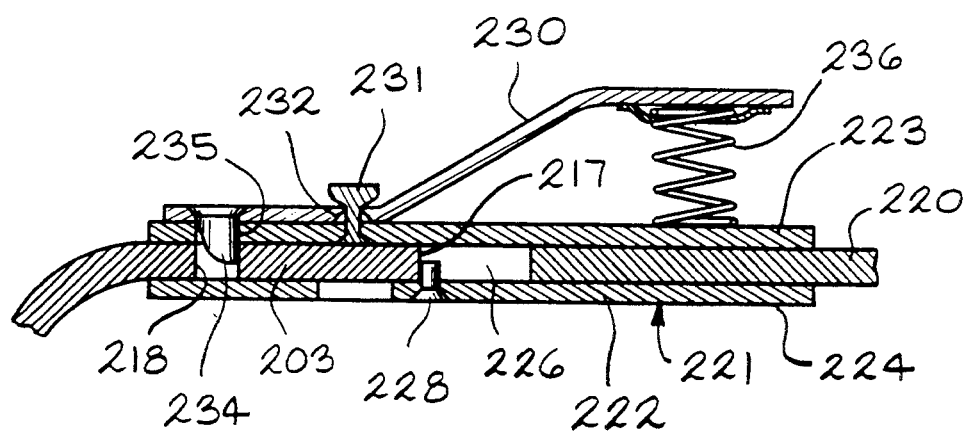
FIG. 30 is a sectional view taken through lines 30—30 of FIG. 26.

A lever 230 is mounted on the upper wall 223 by means of a pivot bar 231 affixed to the upper wall 223 as by enlarging the interior end adjacent the passageway as shown in FIG. 30. The lever 230 is provided with an elongated aperture 232 through which the pivot bar 231 extends.

The portion of the lever 230 adjacent the end of the housing 222 intended to receive the attachment section 203 is substantially planar and has a detent 234 extending downwardly toward the housing 222. The upper wall 223 of the housing 222 is provided with an aperture 235 sized and positioned to receive the detent 234 when the lever 230 is in the position shown in FIG. 30 with the planar portion adjacent the receiving end resting upon the top of the upper wall 223. When the lever is in the position shown is FIG. 30, and the attachment section 203 is positioned therein with its end 217 engaging the stop 228, the aperture 218 of the attachment section 203 will be aligned with the aperture 235 of the upper wall 223. As can be seen in FIG. 30, the detent 234 will extend into the aperture 218 and thus, firmly retain he attachment section 203 in engagement with the housing 222 and the gripping element 220 mounted thereon. A compression spring 236 is positioned near the end of the housing 222 from which the gripping element 220 extends and is between the upper wall 223 and the end of the lever 230 on the opposite side of the pivot bar 231 from the detent 234. The spring 236 thus yieldingly urges such end of the lever 230 away from the upper wall 223 and the portion of the lever 230 on the opposite side of the pivot 230 bar against he upper wall 223 with the detent 234 in the aperture 235 of the upper wall 223 and in the aperture 218 of the attachment section 203.

Figure 4:
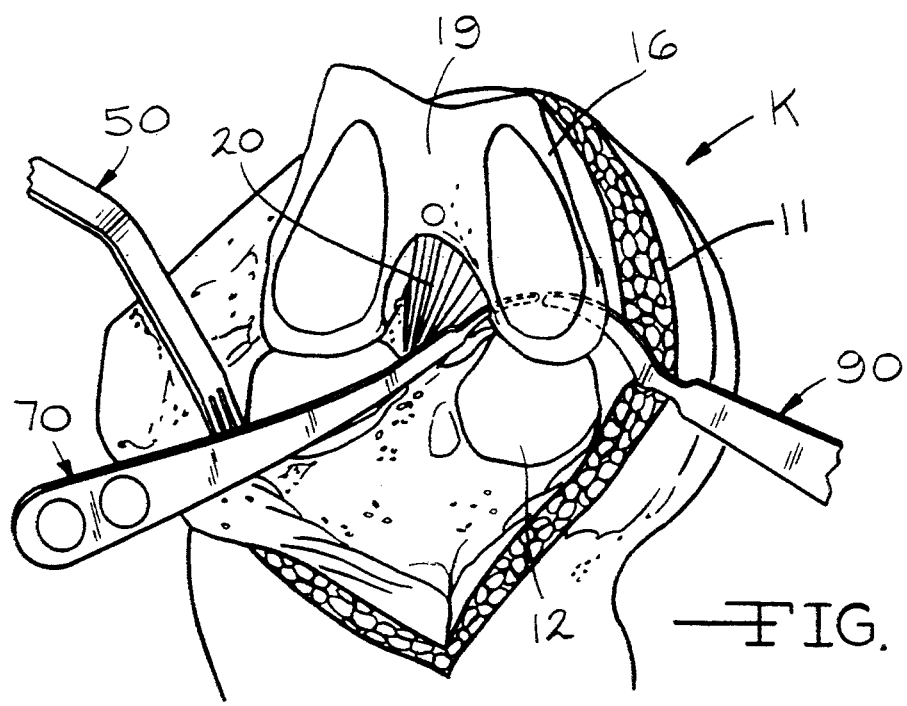
FIG. 4 is a perspective view taken from the front of a knee during surgery showing the step of using the lateral patellar retractor, the posterior cruciate ligament retractor and the collateral ligament retractor.

When it is desired to release the attachment section 203 and the rest of the retractor element 201 from the handle 202, it is necessary for the surgeon or nurse to simply depress the end of the lever 230 against the spring 236. Such movement will lift the detent 234 out of the aperture 218 and permit the attachment section 203 to be removed from the housing 222 as shown in FIG. 4.

The lateral patellar retractors shown in the embodiments of FIGS. 10–12 and 23–35 require that the handle be held in position when the retractor is being used during surgery for its intended purpose. The handle may be held in position by one of the surgical nurses or by fastening weights to the end of the handle. In either case, there is the possibility that .he handle might interfere with the surgical procedure being performed by the surgeon. This risk is eliminated by the present embodiment of FIGS. 26–36. However, it is important, that the retractor element 201 be retained in the proper position after removal of the handle 202 therefrom. This is accomplished by providing a plurality of spikes received in guide/retention members affixed to the support section 204. As may be seen in FIGS. 26–28, a central guide/retention member 240 is affixed to the central portion of the support section 204 immediately above the prongs 206. The central guide/retention member 240 is tubular and has a passageway 241 so positioned that an spike or pin extending therethrough will extend between the prongs 206.

A second guide/retention member 242 is pivotally mounted on one of the edges 214 of the support section 204 and a third guide/retention member 244 is pivotally mounted on the other edge 214. Both the second guide/retention member 242 and the third guide/retention member 244 are aligned with the central guide/retention member 240 with respect to the distance from the tips 215 of the prongs 206. The second guide/retention member 242 has a passageway 243 and the third guide/retention member has a passageway 245 each of which is substantially parallel to the passageway 241 of the central guide/retention member. The second and third guide/retention members 242 and 244 are pivotally mounted on hinges 246 mounted on the opposing edges 214 of the support section 204. Thus, as may be seen in phantom lines in FIG. 28, the third guide/retention member 244 may be pivoted throughout positions of more than 180°. The second guide/retention member may similarly be pivoted to the desired position as determined by the surgeon.

A pair of retention Dins 248 are sized to be slideably received in the passageways 241 and 243 or 241 and 245. Thus, it is normally necessary to provide only two retention pins; however, three guide/retention members 240, 242 and 244 are provided. The reason for this will be described later.

Figure 32:
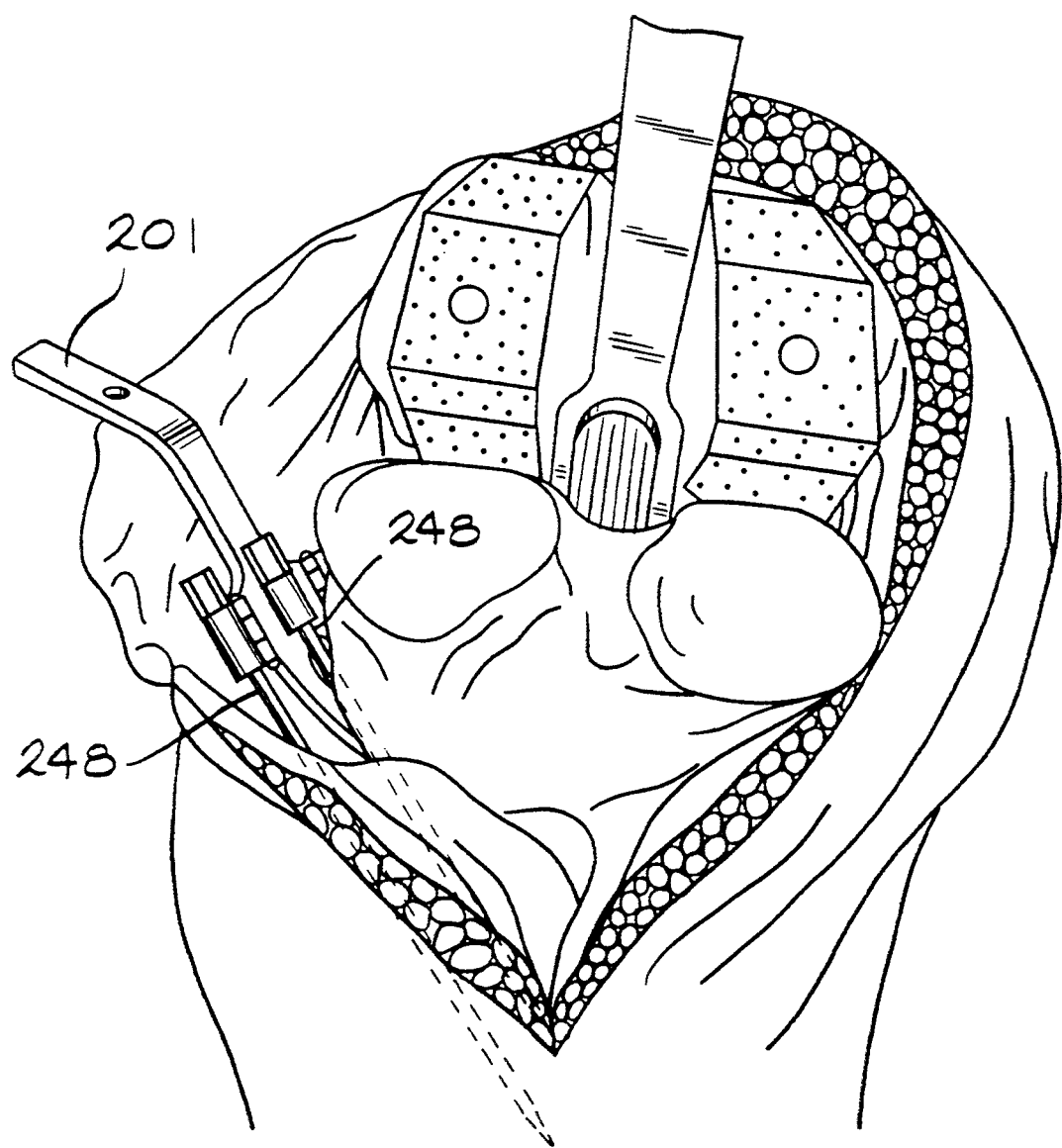
FIG. 32 is a view similar to FIG. 31 showing the handle removed and the anchoring pins holding the retractor element in position.

In performing surgery, the surgeon will position the retractor element 201 to slide around the lateral tibial condyle with minimum damage to the surrounding tissue. The retractor element 201 will be positioned by the surgeon so that a retention pin 248 extending through the passageway 241 of central guide/retention member 240 may be anchored in position without damaging nerves or causing undue damage to other portions of the bone or surrounding soft tissue. The length of the pin 248 is sufficient to provide a firm anchor when it is so positioned. As will be appreciated, if the second guide/retention member 242 were rigidly connected to the support section 204, the possibility would exist that sensitive tissue could be damaged upon affixing the pin 248 through the passageway 243. However, since the second guide/retention member 242 is pivotally mounted, the surgeon may rotate it in order to locate the pin 248 extending therethrough in a position which will cause the least amount of damage to the bone and surrounding soft tissue. As can be seen in FIG. 32, following placement of the pins 248 in anchoring position, the handle 202 may be removed as the pins will retain the retractor element 201 in the proper position for the surgeon to complete the surgical procedure for which retractors are required. Upon completion of such surgical procedure, the pins 248 and then the retractor element 201 may be removed.

Figure 31:
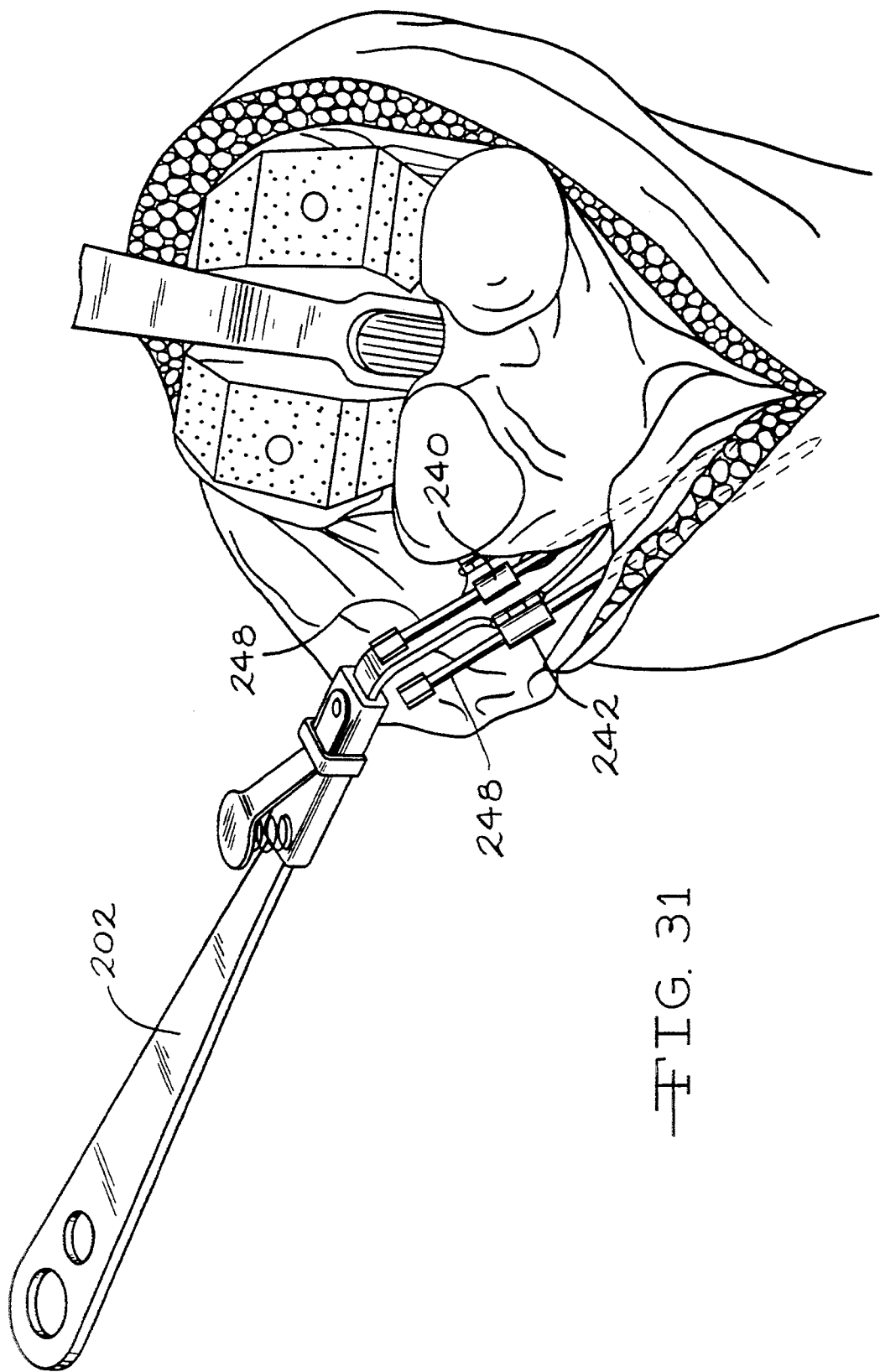
FIG. 31 is a perspective view showing the lateral patellar retractor of the present embodiment in use during surgery with the handle affixed and with retention pins positioned for anchoring.

In FIGS. 31 and 32, the retractor element 201 is shown positioned on the lateral side of the patient's knee. During the surgery, it may also be necessary for the surgeon to retract tissue on the medial side of the knee;. In that event, the surgeon will utilize the pins 248 in the central guide/retention member 240 and in the third guide/retention member 244.

Figure 33:
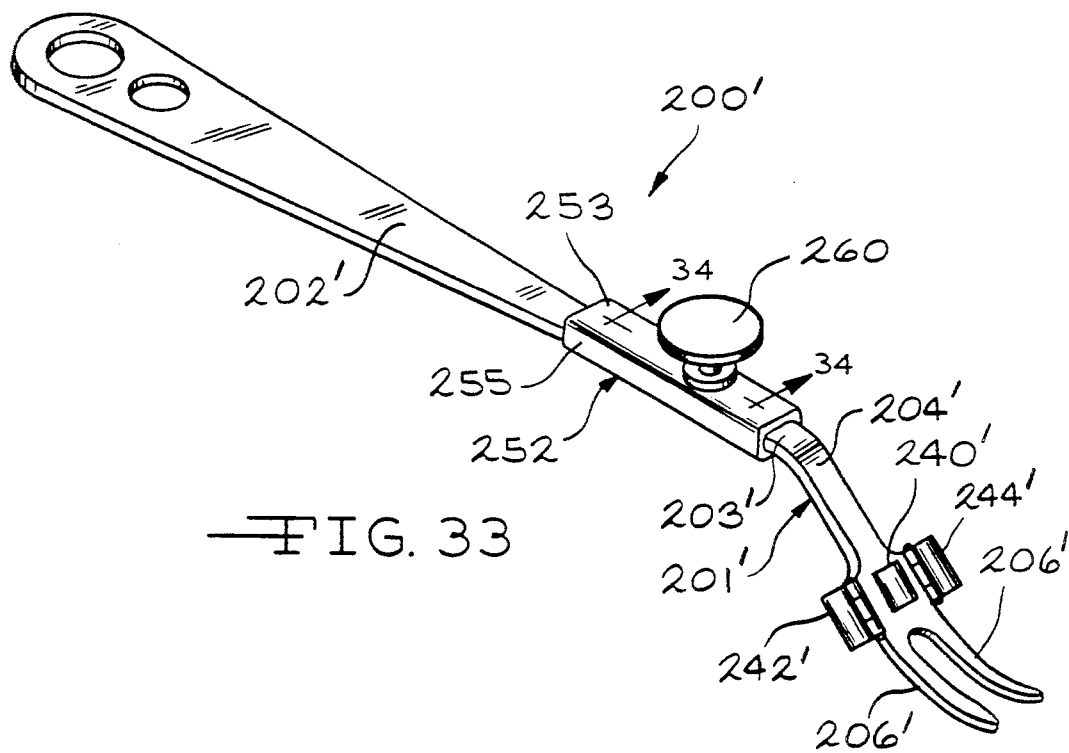
FIG. 33 is a perspective view of a lateral patellar retractor with a detachable handle showing modified means for securing the handle to the retractor element.

Referring now to FIG. 33, there is shown a modified lateral patellar retractor 200'. This modified lateral patellar retractor is similar to the retractor disclosed it, FIGS. 26–30 with the exception of a different type of means for fastening the handle 202' to the retractor element 201' In this embodiment, the handle 202' has a housing 252 permanently fastened thereto. The housing 252 has an upper wall 253, a lower wall 254 and edges 255 cooperating to define a passageway 256.

The retractor element 201' has and attachment section 203' and a support section 204' from which extend a pair of prongs 206'. The attachment section 203' is sized to be slideably received in the end of the passageway 256 and terminates at an end 257. Stop means 258 are positioned in the lower wall 254 to limit the extend to which the opposing end 257 of the retractor element 201' may be inserted in the passageway.

The upper face of the retractor element 201' in the vicinity of the opposing end 257 is provided with a recess 259. A threaded thumb screw 260 is engaged to a plate 261 affixed to the upper wall 253. The thumb screw 260 has a threaded shank which is threadedly engaged to the plate 261 and is received in an aperture 263 in the upper wall 253. The retractor element 201' is secured to the handle 202' by rotating the thumb screw 260 to a position in which the end of the threaded shank 262 engages the recess 259 of the support section 204'.

During surgery, after positioning the lateral patellar retractor 200' in the surgical opening, and affixing it in position with pins in the guide/retention members 240' and 242' or 240' and 244', the thumb screw 260 is rotated to release the handle 202' and its housing 252 from the retractor element 201'.

Figure 34:
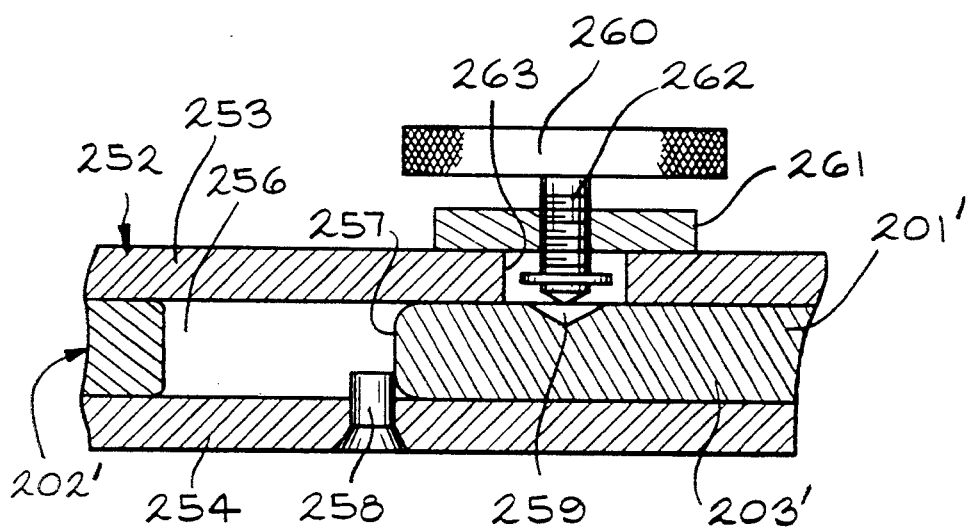
FIG. 34 is a sectional view taken through lines 34—34 of FIG. 33.

Although less desirable, it is within the contemplation of present invention that the housing 222 of the embodiment of FIGS. 26–30 or the housing 252 of the embodiment of FIGS. 33 and 34 be permanently secured to the retractor element 201 or 201' and that the handle 202 or 202' be releasable therefrom.

Referring now to FIGS. 35 and 36, there is shown another embodiment of the lateral patellar retractor of the present invention. Under this embodiment there is provided a lateral patellar retractor 270 having a retractor element 271 and a detachable handle 272 with a connecting element 221 having a housing 273 and release mechanism similar to that described in the embodiment of FIGS. 26–30. Under this embodiment, there; is provided a support section 274 from which extend a pair of spaced apart prongs 275. The prongs 275 are upwardly curved following a radius similar to that set forth in the embodiment of FIGS. 26–30. Additionally, the configuration and size of the prongs 275 are similar to that described with respect to the embodiment of FIGS. 26–30. However, under this embodiment, the portion of the support section 274 between the guide/retention members 240, 242 and 244, and the end to be engaged in the connecting element 221 follows a much gentler arcuate path than that set forth in the embodiment of FIGS. 26–30. Thus, while the radius of curvature of the curved portion 216 of the embodiment of FIGS. 26–30 is 0.5 inch±0.030 inch, the radius of curvature for the support section 274 portion designated 276 in FIG. 35 is 0.8 inch±0.1 inch. Additionally, the portion of the handle 278 extending beyond the connecting element 221 is curved rather than planar.

The retractor of the present invention is one which permits efficient utilization of surgical personnel by firmly affixing in place the retractor element without the necessity of utilizing personnel to hold the retractors in position during the surgical procedure or the utilization of cumbersome weights to hold them in position. Additionally, removal of the handles gives the surgeon better access to the surgical site in order to permit an unobstructed access thereto.

The invention disclosed herein provides new and novel surgical instruments in the form of retractors and femoral distractor which provide maximum protection to critical soft tissue members during osteotomy and other procedures and permit new and effective surgical procedures to be performed.

I claim:

1. A lateral patellar retractor for use in performing knee surgery comprising:

(a) a pair of spaced apart prongs having parallel outer edges, each of said outer edges lying respectively in a first plane and a second plane, said first plane and said second plane being parallel, spaced apart inner edges and upper and lower surfaces following a curved path such that the upper surface is concave and the lower surface is convex, each of said prongs terminating in a tip, the radius of curvature for the curved path followed by said upper surface being 3.31 inches±0.030 inch, the distance between said outer edges being 0.770 ±0.030 inch, and the minimum distance between said inner edges being no less than 0.400;

(b) a support section integral with said prongs, said support section having upper and lower surfaces which include opposing portions following a curved path such that the upper surface is convex and the lower surface is concave; and (c) a handle joined to said support section.

2. A lateral patellar retractor according to claim 1, wherein the center of said radius of curvature is positioned on the opposite side of said tips from said handle and above said handle.

3. A lateral patellar retractor for use in performing knee surgery comprising:
(a) a pair of spaced apart prongs having parallel outer edges each of said outer edges lying respectively in a first plane and a second plane, said first plane and said second plane being parallel, spaced apart inner edges and upper and lower surfaces following a curved path such that the upper surface is concave and the lower surfaces, convex, each of said prongs terminating in a tip
(b) a support section integral with said prongs, said support section having upper and lower surfaces which include opposing portions following a curved path such that the upper surface is convex and the lower surface is concave;
(c) a handle; and
(d) a releaseable connector connecting said handle to said support section including a housing affixed to said handle having a passageway for receiving said support section, engagement means on the portion of support section received in said passageway, and means on said housing engageable with said engagement means.

4. A lateral patellar retractor according to claim 3, wherein said engagement means comprises a recess.

5. A lateral patellar retractor according to claim 3, further including stop means on said housing for limiting the extent to which said support section may be inserted in said housing.

6. A lateral patellar retractor according to claim 4, further including a lever on said housing having a detent engageable with said recess and means yieldingly urging said lever to position said detent into said recess.

7. A lateral patellar retractor according to claim 3, wherein said engagement means includes a screw mounted on said housing and means for rotating said screw from a first position spaced from said support section to a second position engaged with said support section.

8. A lateral patellar retractor according to claim 3, further including guide means mounted on said support section.

9. A lateral patellar retractor according to claim 7, wherein said guide means include a first tubular member affixed to said support section, said first tubular member including a first guide passageway having a longitudinal axis which extends between said prongs.

10. A lateral patellar retractor according to claim 9, wherein said guide means include a second tubular member and a hinge rotatably mounting said tubular member to said support member.

11. A lateral patellar retractor according to claim 9, wherein said guide means include second and third tubular members and hinges rotatably mounting each of said second and third tubular members to said support member, said second and third tubular members being positioned on opposite sides of said longitudinal axis.

12. A lateral patellar retractor according to claim 8 further including retention pins engageable with said guide means for retaining said prongs and support section in a predetermined position.

13. A lateral patellar retractor for use in performing knee surgery comprising:
(a) a retractor element including
(i) a pair of spaced apart prongs having upper and lower surfaces following a curved path such that the upper surface is concave and the lower surface is convex, each of said prongs terminating in a tip;
(ii) a support section integral with said prongs, said support section having upper and lower surfaces which include a portion following a curved path such hat the upper surface is convex and the lower surface is concave; and
(iii) guide means mounted On said support section; the radius of curvature for the curved path followed by said upper surface being 3.31 inches±0.030 inch, the distance between said outer edges being 0.770 inch±0.030 inch, and the minimum distance between said inner edges being no less than 0.400 inch;
(b) a handle; and
(c) connector means for detachably fastening said handle to said retractor element.

14. A lateral patellar retractor according to claim 13, wherein the center of said radius of curvature is positioned on the opposite side of said tips from said handle and above said handle.

15. A lateral patellar retractor for use in performing knee surgery comprising:
(a) a retractor element: including
(i) a pair of spaced apart prongs having upper and lower surfaces following a Curved path such that the upper surface is concave and the lower surface is convex., each of said prongs terminating in a tip;
(ii) a support section integral with said prongs, said support section having upper and lower surfaces which include a portion following a curved path such that the upper surface is convex and the lower surface is concave; and
(iii) guide means mounted on said support section said guide means including a first tubular member affixed to said support section, said first tubular member including a first guide passageway having a longitudinal axis which extends between said prongs;
(b) a handle; and
(c) connector means for detachably fastening said handle to said retractor element.

16. A lateral patellar retractor according to claim 15, wherein said support section includes a pair of parallel edges extending between said upper and lower surfaces and said guide means include a second tubular member, said second tubular member positioned outwardly from one of said edges.

17. A lateral patellar retractor according to claim 15, wherein said guide means include a second tubular member rotatably mounted to said support member.

18. A lateral patellar retractor according to claim 15, wherein said guide means include second and third tubular members, each of said second and third tubular members being rotatably mounted to said support member.

19. A lateral patellar retractor for use in performing knee surgery comprising:
(a) a retractor element including
(i) a pair of spaced apart prongs having upper and lower surfaces following a curved path such that the upper surface is concave and the lower surface is convex, each of said prongs having a thickness no greater than 0.135 inch and terminating in a tip 2

(ii) a support section integral with said prongs, said support section having upper and lower surfaces which include a portion following a curved path such that the upper surface is convex and the lower surface is concave; and (iii) guide means mounted on said support section;

(b) a handle; and (c) connector means for detachably fastening said handle to said retractor including a housing affixed to said handle having a passageway for receiving said support section, engagement means on the portion of support section received in said passageway, and means on said housing engageable with said engagement means.

20. A lateral patellar retractor according to claim 19, further including stop means on said housing for limiting the extent to which said support section may be inserted in said housing.

21. A lateral patellar retractor according to claim 19, further including a lever on said housing having a detent engageable with said recess and means yieldingly urging said lever to position said detent into said recess.

22. A lateral patellar retractor according to claim 19, wherein said engagement means includes a screw mounted on said housing and means for rotating said screw from a first position spaced from said support section to a second position engaged with said support section.

23. A lateral patellar retractor for use in performing knee ,Surgery comprising:

(a) a handle;

(b) an arcuate section extending from said handle and following a curved path joining said handle;

(c) an integral support extending from said arcuate section and disposed at an angle of 55°±30° to a horizontal plane when the portion of said handle closest thereto is positioned in a horizontal plane; and (d) a pair of spaced apart prongs extending from said integral support and following a path which includes a curve which is reverse in direction to the curved path of said arcuate section, said integral prongs each terminating in a tip, wherein the portion of each of said prongs adjacent said tip has a planar upper surface and a lower surface which tapers toward said upper surface as it approaches said tip and wherein the portion of said prongs having a planar upper surface extends for a distance of 0.50 inch±0.030 inch.

24. A lateral patellar retractor according to claim 23, wherein said integral support has a portion adjacent said arcuate section which is flat.

25. A surgical retractor comprising:

(a) a retractor element having:

(i) a support section;

(ii) an engagement section extending from said support section to a first end;

(iii) a prong section extending from said support section to a second end opposite said first end;

(iv) retention means for holding said retractor element in a fixed position said retention means comprising a plurality of tubular members affixed to said support section;

(b) a handle element; and (c) means for detachably securing said handle element to said engagement section.

26. A surgical retractor comprising:

(a) retractor element having (i) a Support section (ii) an engagement section extending from said support section to a first end;

(iii) a prong section extending from said support section to a second end opposite said first end;

(iv) retention means for holding said retractor element in a fixed position said retention means comprising a plurality of tubular members affixed to said support section, at least one of said tubular support members being rigidly affixed and at least one of said tubular member being adjustably affixed;

(b) a handle element; and (c) means for detachably securing said handle element to said engagement section.

27. A surgical retractor comprising:

(a) a retractor element having:

(i) a support section;

(ii) an engagement section extending from said support section to a first end;

(iii) a prong section extending from said support section to a second end opposite said first end said prong section including a pair of spaced apart prongs (iv) retention means mounted on said support section for holding said retractor element in a fixed position, said retention means including a first tubular member rigidly affixed to said support section and having a longitudinal axis lying in a plane spaced midway between said prongs and a second tubular member adjustably affixed to said support section;

(b) handle element; and (c) means for detachably securing said handle element to said engagement section.

28. A surgical retractor comprising:

(a) a retractor element having:

(i) a support section;

(ii) an engagement section extending from said support section to a first end;

(iii) a prong section extending from said support section to a second end opposite said first end;

(iv) retention means mounted on said support section for holding said retractor element in a fixed position;

(b) a handle element; and (c) means for detachably securing said handle element to said engagement section said means for detachably securing said handle element to said engagement section comprises a housing affixed to said handle element having a passageway for receiving said engagement section, engagement means on the portion of engagement section received in said passageway, and means on said housing engageable with said engagement means.

29. A surgical retractor according to claim 28, wherein said engagement means comprises a recess.

30. A surgical retractor according to claim 28, further including stop means on said housing for limiting the extent to which said engagement section may be inserted in said housing passageway.

31. A surgical retractor according to claim 29, further including a lever on said housing having a detent engageable with said recess and means yieldingly urging said lever to position and detent into said recess.

32. A surgical retractor according to claim 28, wherein said engagement means includes a screw mounted on said housing and means for rotating said screw from a first position spaced from said engagement section to a second position engaged with said engagement section.

33. A method of performing knee surgery comprising the steps of:
(a) incising exterior portions of the knee to gain access to the interior;
(b)
(i) inserting a lateral patellar retractor having a detachable handle and a plurality of spaced apart prongs extending from a common support into the incised knee, at least one of said lateral patellar retractor prongs engaging the lateral tibial condyle and the common support engaging the incised soft tissue;
(ii) moving said common support laterally against said soft tissue to a desired position;
(iii) securing said lateral patellar retractor in said desired position
(iv) removing said handle; and
(c) performing tibial osteotomy while said lateral patellar retractor is maintained secured in said desired position.

34. A method of performing knee surgery comprising the steps of:
(a) incising exterior portions of the knee to gain access to the interior;
(b)
(i) inserting a retractor having a detachable handle and at least one prong extending from a support into the incised knee, said at least one prong engaging tissue adjacent bony structure of said knee and the support engaging the incised soft tissue;
(ii) moving said support against said soft tissue to a desired position;
(iii) securing said retractor in said desired position;
(iv) removing said handle; and
(c) performing osteotomy while said retractor is maintained secured in said desired position.

35. A method of performing knee surgery comprising the steps of:
(a) incising exterior portions of the knee to gain access to the interior;
(b) providing a surgical retractor having
(i) a retractor element including
(A) a support section;
(B) an engagement section extending from said support section to a first end,
(C) a prong section extending from said support section in an area opposite said engagement section
(D) retention means for holding said retractor element in a fixed position;
(ii) a handle element;
(iii) means for detachably securing said handle element to said engagement section; and
(iv) anchoring means engageable with said retention means;
(c)
(i) inserting said retractor into the incised knee with said prong section engaging tissue adjacent bony structure of said knee and said support section engaging the incised soft tissue;
(ii) moving said support section against said soft tissue to a desired position;
(iii) engaging said anchoring means to said retention means and to the interior of said incised knee to secure said retractor element in said desired position;
(iv) removing said handle; and
(d) performing tibial osteotomy while said retractor element is maintained secured in said desired position.

36. A method of performing knee surgery comprising the steps of:
(a) incising exterior portions of the knee to gain access to the interior;
(b) providing a surgical retractor having
(i) a retractor element having
(A) a support section;
(B) an engagement section extending from said support section to a first end;
(C) a prong section extending from said support section in an area opposite said engagement section;
(D) retention means including a plurality of tubular members affixed to said support section, at least one of said tubular members being rigidly affixed and at least one of said tubular members being adjustably affixed;
(ii) a handle element;
(iii) means for detachably securing said handle element to said engagement section and anchoring means engageable with said retention means; and
(iv) anchoring means engageable with said retention means;
(c)
(i) inserting said retractor into the incised knee with said prong section engaging tissue adjacent bony structure of said knee and said support section engaging the incised soft tissue;
(ii) moving said common support laterally against said soft tissue to a desired position;
(iii) engaging said anchoring means to said rigidly affixed tubular member; and
(iv) adjusting said adjustable tubular member and engaging said anchoring means thereto to secure said retractor;
(v) removing said handle; and
(d) performing tibial osteotomy while said lateral patellar retractor is maintained secured in said desired position.

* * * * *

UNITED STATES PATENT AND TRADEMARK OFFICE
CERTIFICATE OF CORRECTION

PATENT NO. : 5,380,331
DATED : January 10, 1995
INVENTOR(S) : W.E. Michael Mikhail It is certified that error appears in the above—identified patent and that said Letters Patent is hereby corrected as shown below:

In column 3, line 65, "The" should be --the--.

In column 4, line 48, "Toward" should be --toward--.

In column 6, line 16-17, "54'" should be --54"-- and "55'" should be --55"--.

In column 7, line 45, "0,020" should be --0.020--.

In column 7, line 53, "78," should be --78.--.

In column 9, line 10, "The" should be --the--.

In column 11, line 47, "C" should be --$C_1$--.

In column 12, line 48, "The" should be --the--.

In column 13, line 66, "he" should be --the--.

In column 14, line 8, "he" should be --the--.

In column 14, line 60, "Dins" should be --pins--.

In column 18, line 7, "hat" should be --that--.

In column 18, line 9, "On" should be --on--.

In column 18, line 27, "Curved" should be --curved--.

Column 18, line 68, "tip 2" should be --tip;--

UNITED STATES PATENT AND TRADEMARK OFFICE
CERTIFICATE OF CORRECTION

PATENT NO. : 5,380,331
DATED : Jan. 10, 1995
INVENTOR(S) : W.E. Michael Mikhail

It is certified that error appears in the above-indentified patent and that said Letters Patent is hereby corrected as shown below:

Column 20, line 1, "Support" should be —support—.

Signed and Sealed this

Thirtieth Day of January, 1996

Attest:

BRUCE LEHMAN

Attesting Officer

Commissioner of Patents and Trademarks